US008617622B2

(12) United States Patent
Armani et al.

(10) Patent No.: US 8,617,622 B2

(45) Date of Patent: Dec. 31, 2013

(54) **EXTRACTS AND COMPOUNDS FROM *FICUS BENGHALENSIS* FOR INCREASING HAIR GROWTH AND DECREASING HAIR LOSS**

(75) Inventors: Antonio Armani, Richmond Hill (CA); Sara Armani, Richmond Hill (CA); Charitha Seneviratne, Mississuaga (CA); Reza Nazari, Richmond Hill (CA)

(73) Assignee: 8583765 Canada Inc., Mississauga, Ontario (CA)

( * ) Notice: Subject to any disclaimer, the term of this patent is extended or adjusted under 35 U.S.C. 154(b) by 147 days.

(21) Appl. No.: 13/051,543

(22) Filed: Mar. 18, 2011

(65) Prior Publication Data

US 2012/0128796 A1 May 24, 2012

Related U.S. Application Data

(60) Provisional application No. 61/315,729, filed on Mar. 19, 2010, provisional application No. 61/379,915, filed on Sep. 3, 2010.

(51) Int. Cl.
*A61K 36/00* (2006.01)

(52) U.S. Cl.
USPC .......................... 424/773; 424/725; 424/401

(58) Field of Classification Search
None
See application file for complete search history.

(56) References Cited

U.S. PATENT DOCUMENTS

| | | | | |
|---|---|---|---|---|
| 5,723,149 | A * | 3/1998 | Bonte et al. | 424/450 |
| 6,124,362 | A | 9/2000 | Bradbury et al. | |
| 6,482,857 | B1 | 11/2002 | Bradbury et al. | |
| 2002/0183297 | A1 | 12/2002 | Niazi | |
| 2004/0071652 | A1 | 4/2004 | Dupuis et al. | |
| 2004/0156920 | A1 | 8/2004 | Kane | |
| 2008/0206373 | A1 | 8/2008 | Millikin et al. | |

FOREIGN PATENT DOCUMENTS

| | | | |
|---|---|---|---|
| JP | 63243017 | A * | 10/1988 |
| WO | WO 99/56545 | * | 11/1999 |

OTHER PUBLICATIONS

Ao (International Journal of Food Science and Technology (Feb. 2009), vol. 44, pp. 349-358).*

Shah (Electronic Journal of Environmental, Agricultural and Food Chemistry (2008), vol. 7, No. 14, pp. 2743-2748).*

Suresh, S. Babu and Madhavi, M. "Green Remedies: Healing Power of Herbs." Pustak Mahal, Delhi, Nov. 2003, p. 54.

Patil, D.A. "Healthcare and Origins of Folkloric Medicines in North Maharashtra." International Symposium—Underutilized plants for food, nutrition, income and sustainable development, Arusha, Tanzania, Mar. 3-7, 2008. Available online: http://www.icuc-iwmi.org.com/Symposium2008/Theme 2/T2-9-Patil.pdf.

The Indian Company Pan Herbbo Limited. "Herbo Keshamrut Herbal Hair Oil." Available online: http://www.en2s.com/files/keshamrut.htm (accessed Oct. 23, 2009).

Anne, J. "Hair Loss Remedies—Simple Ayurvedic Treatments." Ezine Articles. Available online: http://ezinearticles.com/?Hair-Loss-Remedies—Simple-Ayurvedic-Treatments&id=488224 (Mar. 14, 2007).

Chiang, Y. M., et al., 2005 Phytochemistry 66:495-501.

Chiang, Y.M., et al., 2001 J. Nat. Prod. 64:436-439.

Mejin, M. Feb. 2009, BSc Thesis, University of Adelaide, Australia.

Chiang Y. M. et al., 2005 Phytochemistry 66:495-501.

Chiang Y. M. et al., 2001 J. Nat. Prod. 64:436-439.

Mejin M., Feb. 2009, BSC Thesis, University of Adelaide, Australia.

Khan (Indian Journal of Pharmaceutical Sciences (2008)), vol. 70, No. 3, pp. 287-291.

* cited by examiner

*Primary Examiner* — Susan Hoffman

(74) *Attorney, Agent, or Firm* — Ballard Spahr LLP

(57) ABSTRACT

This application discloses natural product extracts and compounds from an aerial root of a *Ficus* plant, such as *Ficus benghalensis*. The application also discloses the use of natural product extracts and compounds from *Ficus* plants for increasing hair growth and decreasing hair loss. Methods of producing the extracts and isolating the compounds are further disclosed.

18 Claims, 20 Drawing Sheets

Thickened hair

New hair

Both new and thickened hair

Thickened hair

New hair

Both new and thickened hair

Thickened hair

New hair

Both new and thickened hair

Thickened hair

New hair

Both new and thickened hair

EXTRACTS AND COMPOUNDS FROM *FICUS BENGHALENSIS* FOR INCREASING HAIR GROWTH AND DECREASING HAIR LOSS

CROSS REFERENCE TO RELATED APPLICATIONS

This non-provisional application claims priority from U.S. provisional application No. 61/315,729 filed on Mar. 19, 2010 and U.S. provisional application No. 61/379,915 filed on Sep. 3, 2010, both of which are incorporated herein by reference in their entirety.

FIELD

This application discloses natural product extracts and compounds from an aerial root of a *Ficus* plant, such as *Ficus benghalensis*, that are useful for increasing hair growth and decreasing hair loss in mammals. Methods of producing the extracts and isolating the compounds are also disclosed.

BACKGROUND

Hair Loss

Genetic pattern hair loss affects approximately one-half of the world's male population and more than one-quarter of the female population. Current treatments for hair loss include surgical hair restoration and pharmaceutical interventions.

Small organic compounds are currently sold for treating hair loss. These compounds have shown limited results. For example, the oral medication finasteride is used to treat balding. However, as finasteride affects serum DHT levels, it can lead to numerous side effects. The topical lotion minoxidil is also used to arrest the progression of hair loss.

There remains a need for naturally-sourced products for treating hair loss. A natural formulation to treat hair loss and promote hair growth with minimal side effects is highly desirable.

Hair Follicles

All parts of the hair follicle are cyclically re-generated. The hair follicle is an entirely epidermally derived structure (including the sebaceous gland) and is produced by epidermal stem cells (eSC) residing in the epidermal bulge. Cross talk between mesenchyma derived dermal papilla (DP) cells and the epidermal eSC is crucial for cell differentiation and proliferation (Morris, 2004; Blanpain and Fuchs, 2006).

Balding, or hair loss, is a consequence of hair follicle miniaturization. Normally, a hair follicle cycles through phases including the anagen (growth) phase, the catagen (transition) phase and the telogen (resting or quiescent) phase. In the miniaturization process, the hair follicle enters a prolonged lag phase following the telogen stage. Thus, one aim of hair loss therapies is to push or coax the hair follicle after telogen to quickly enter anagen similar to a normal hair follicle (Cotsaleris and Millar, 2001).

In addition, since the length and size of the hair depends on the length of the anagen phase and size of the hair follicle respectively, another way to promote hair growth is to use compounds that prolong the length of the anagen phase and increase hair follicle size.

SUMMARY OF THE DISCLOSURE

The invention relates to a method of producing an extract, its fractions, sub-fractions and compounds from an aerial root portion of a *Ficus* plant, optionally *Ficus benghalensis*, where the extract and its fractions, sub-fractions and compounds are useful as hair growth-increasing agents and/or hair loss-decreasing agents. The aerial root portion optionally comprises an aerial root tip. The method typically involves preparing a crude extract of an aerial root portion of a *Ficus* plant, optionally the aerial root tip, and fractionating the crude extract with at least one solvent to obtain various fractions.

The invention also relates to a method where the solvent is selected from the group consisting of n-hexane, dichloromethane, ethyl acetate, methanol and water.

The invention further relates to a method where a series of fractions are obtained by:

(a) performing a n-hexane extraction on the crude extract to obtain a n-hexane fraction and a first residue, (b) performing a dichloromethane extraction on the first residue to obtain a dichloromethane fraction and a second residue, (c) performing an ethyl acetate extraction on the second residue to obtain an ethyl acetate fraction and a third residue, (d) performing a methanol extraction on the third residue to obtain a methanol fraction and a fourth residue, and (e) performing a water extraction on the fourth residue to obtain a water fraction.

In one embodiment of the invention, the method further comprises sub-fractionating the n-hexane fraction to obtain at least one sub-fraction. The n-hexane sub-fraction is optionally sub-fractionated using chromatography, solvent partitioning or any other method known in the art or any combination thereof.

In one embodiment of the invention, the methods described above involve the further step of topically administering one or more of the fractions and/or sub-fractions to a mammal to increase hair growth on the mammal or to decrease hair loss on the mammal.

In another embodiment, the methods involve the further step of exposing hair follicles in vitro to one or more of the fractions to increase the viability of the hair follicles. In another embodiment, the methods involve the further step of exposing hair follicles in vivo to one or more of the fractions to increase the viability of the hair follicles. In another embodiment, the methods involve the further step of exposing hair follicle cells, in vivo or in vitro, to one or more of the fractions to increase the viability of the hair follicle cells.

In a further embodiment of the method, the *Ficus* is *Ficus benghalensis.*

In another embodiment of the method, the method further comprises the use of the ethyl acetate fraction to increase the viability of hair follicle cells, optionally outer root sheath cells or epidermal stem cells. The hair follicle cells are optionally cells in vitro or in vivo. In another embodiment, the method comprises the use of the ethyl acetate fraction to rejuvenate skin.

The invention also relates to the use of a crude extract, optionally a total aqueous extract, of an aerial root portion, optionally an aerial root tip, of a *Ficus* plant, optionally *Ficus Benghalensis*, for increasing hair growth, decreasing hair loss, rejuvenating skin, increasing the viability of a hair follicle, or increasing the viability of a hair follicle cell.

The invention further relates to an ethyl acetate fraction from a crude extract of an aerial root portion, optionally an aerial root tip, of a *Ficus* plant, optionally *Ficus Benghalensis*, wherein the fraction is obtained by a. performing a n-hexane extraction on the crude extract to obtain a n-hexane fraction and a first residue, b. performing a dichloromethane extraction on the first residue to obtain a dichloromethane fraction and a second residue, and c. performing an ethyl acetate extraction the second residue to obtain an ethyl acetate fraction.

The invention also relates to the use of the ethyl acetate fraction to increase the viability of hair follicle cells, optionally outer root sheath cells or epidermal stem cells. The invention further relates to the use of the ethyl acetate fraction to rejuvenate skin.

The invention also relates to a fraction from a crude extract of an aerial root portion of a *Ficus* plant, optionally the portion comprising an aerial root tip, whereby the fraction is obtained by extracting the crude extract with a solvent having a dielectric constant of 1.1 to 4.0. In another embodiment, the dielectric constant is 1.5 to 2.5.

In a further embodiment, the solvent is n-hexane. In yet another embodiment, the *Ficus* is *Ficus benghalensis*.

The invention further relates to the use of a composition comprising the n-hexane fraction to increase hair growth. In another aspect of the invention, the hair is a hair follicle in vitro or in vivo. The invention also relates to the use of a composition comprising the n-hexane fraction to decrease hair loss or to increase the viability of a hair follicle cell, in vitro or in vivo.

The invention further relates to a composition comprising the n-hexane fraction and a pharmaceutically acceptable carrier. Optionally, the composition comprises 1 μg/ml to 50 μg/ml of the n-hexane fraction, optionally 5 to 15 μg/ml of the n-hexane fraction. The invention also relates to the use of the composition increase hair growth, optionally wherein the hair is a hair follicle in vitro or in vivo. The invention further relates to the use of the composition to decrease hair loss and/or increase the viability of a hair follicle cell. In one embodiment, the n-hexane fraction is for use in an amount of 1 to 100 μg/day, optionally 10 to 30 μg/day.

The invention also relates to a sub-fraction of the n-hexane fraction, wherein the sub-fraction is obtained by (a) sub-fractionating the fraction, and (b) isolating a sub-fraction comprising a compound selected from the group consisting of: cerebrosides, terpenes, saturated fatty acids, unsaturated fatty acids, polar disaccharides, octadecenoic acids, psoralen, coumarins, azelaic acid, waxes, sterols, lupeol, cycloartenol, α-amyrin, saturated ester wax, 5-methoxypsoralen, stigmasterol, β-sitosterol, betulinic acid, betulonic acid, palmitic acid and β-hydroxy-9,11-octadecadieonic acid.

The invention also relates to a sub-fraction of the n-hexane fraction, wherein the sub-fraction is obtained by a. sub-fractionating the fraction, and b. isolating a sub-fraction comprising the following compounds: lupeol, cycloartenol, α-amyrin, saturated ester wax, 5-methoxypsoralen, stigmasterol, β-sitosterol, betulinic acid, betulonic acid, palmitic acid, 13-hydroxy-9,11-octadecadieonic acid and cerebrosides.

In one embodiment, the isolated sub-fraction comprises at least 0.3% by weight lupeol, 0.4% by weight cycloartenol, 0.4% by weight α-amyrin, 0.7% by weight saturated ester wax, 1.2% by weight 5-methoxypsoralen, 5% by weight stigmasterol and β-sitosterol, 0.3% by weight betulinic acid, 0.8% by weight betulonic acid, 0.46% by weight palmitic acid, 0.1% by weight 13-hydroxy-9,11-octadecadieonic acid and 0.4% by weight cerebrosides.

Optionally, the n-hexane fraction is sub-fractioned by solvent partitioning, chromatography or any combination thereof. In one embodiment, the chromatography is high performance liquid chromatography, optionally high performance liquid chromatography with a 19×300 mm C18 column, a gradient elution with 0.1% HCOOH in water and 0.1% HCOOH in acetonitrile and flow rate 18 mL/min.

In another embodiment, the chromatography is vacuum-assisted liquid chromatography, optionally vacuum-assisted liquid chromatography with sequential elution using solvent mixtures from 100% hexane to 100% chloroform to 100% methanol.

The invention also relates to the use of a sub-fraction of the n-hexane fraction to increase hair growth. Optionally, the hair is a hair follicle in vitro or in vivo. The invention further relates to the use of a composition comprising the sub-fraction of the n-hexane fraction to decrease hair loss or to increase the viability of a hair follicle cell, optionally a hair follicle cell in vitro or in vivo.

In another embodiment, the invention relates to the use of a fraction or sub-fraction from a crude extract of an aerial root portion of a *Ficus* plant for increasing hair growth or decreasing hair loss wherein the fraction or sub-fraction comprises a compound selected from the group consisting of: cerebrosides, terpenes, saturated fatty acids, unsaturated fatty acids, polar disaccharides, octadecenoic acids, psoralen, coumarins, azelaic acid, waxes, sterols, lupeol, cycloartenol, α-amyrin, saturated ester wax, 5-methoxypsoralen, stigmasterol, β-sitosterol, betulinic acid, betulonic acid, palmitic acid and 13-hydroxy-9,11-octadecadieonic acid.

In yet another embodiment, the invention relates to the use of a sub-fraction from a crude extract of an aerial root portion of a *Ficus* plant for increasing hair growth or decreasing hair loss wherein the sub-fraction comprises or consists essentially of the following compounds: lupeol, cycloartenol, α-amyrin, saturated ester wax, 5-methoxypsoralen, stigmasterol, β-sitosterol, betulinic acid, betulonic acid, palmitic acid, 13-hydroxy-9,11-octadecadieonic acid and cerebrosides. In another embodiment, the sub-fraction comprises 0.3% by weight lupeol, 0.4% by weight cycloartenol, 0.4% by weight α-amyrin, 0.7% by weight saturated ester wax, 1.2% by weight 5-methoxypsoralen, 5% by weight stigmasterol and β-sitosterol, 0.3% by weight betulinic acid, 0.8% by weight betulonic acid, 0.46% by weight palmitic acid, 0.1% by weight 13-hydroxy-9,11-octadecadieonic acid and 0.4% by weight cerebrosides.

The invention also relates to a composition comprising a plurality of sub-fractions of the n-hexane fraction, wherein the plurality of sub-fractions are obtained by:

(a) partitioning the n-hexane fraction with chloroform to obtain a chloroform partitioned fraction;

(b) loading the chloroform partitioned fraction into a chromatography column, optionally a silica gel vacuum-assisted liquid chromatography column;

(c) eluting the chloroform partitioned fraction through sequential elution using solvent mixtures from 100% hexane to 100% chloroform to 100% methanol to obtain a plurality of sub-fractions;

(d) collecting and combining the plurality of sub-fractions.

The invention also relates to a composition comprising sub-fractions eluted at each of the solvent gradients listed in column 2 of Table 9. In a preferred embodiment, composition does not contain a sub-fraction eluted at 97% chloroform: 3% methanol. In another embodiment, the composition does not contain a sub-fraction comprising unsaturated fatty acids. In another embodiment, the composition does not include a sub-fraction that decreases the viability, optionally by at least 5%, at least 10%, at least 20%, at least 30% or at least 50% of explant hair follicles at 1 μg/ml. In another preferred embodiment, the composition comprises the following compounds: lupeol, cycloartenol, α-amyrin, saturated ester wax, 5-methoxypsoralen, stigmasterol, β-sitosterol, betulinic acid, betulonic acid, palmitic acid, 13-hydroxy-9,11-octadecadieonic acid and cerebrosides. In yet another embodiment, the composition comprises at least 0.3% by weight lupeol, 0.4% by weight cycloartenol, 0.4% by weight α-amyrin, 0.7% by weight saturated ester wax, 1.2% by weight 5-methoxypsoralen, 5% by weight stigmasterol and β-sitosterol, 0.3% by weight betulinic acid, 0.8% by weight betulonic acid, 0.46% by weight palmitic acid, 0.1% by weight 13-hydroxy-9,11-octadecadieonic acid and 0.4% by weight cerebrosides The invention also relates to the use of the composition described above to increase hair growth. Optionally, the hair is a hair follicle in vitro or in vivo. The invention further relates to use of the composition described above to decrease hair loss or to increase the viability of a hair follicle cell, optionally a hair follicle cell in vitro or in vivo.

The invention also relates to a composition comprising lupeol, cycloartenol, α-amyrin, saturated ester wax, 5-methoxypsoralen, stigmasterol, β-sitosterol, betulinic acid, betulonic acid, palmitic acid, 13-hydroxy-9,11-octadecadieonic acid and cerebrosides and to the use of the composition to increase hair growth or decrease hair loss. The invention also relates to a composition consisting essentially of lupeol, cycloartenol, α-amyrin, saturated ester wax, 5-methoxypsoralen, stigmasterol, β-sitosterol, betulinic acid, betulonic acid, palmitic acid, 13-hydroxy-9,11-octadecadieonic acid and cerebrosides and to the use of the composition to increase hair growth or decrease hair loss. Optionally, the composition comprises at least 0.3% lupeol, 0.4% cycloartenol, 0.4% α-amyrin, 0.7% saturated ester wax, 1.2% 5-methoxypsoralen, 5% stigmasterol and 13-sitosterol, 0.3% betulinic acid, 0.8% betulonic acid, 0.46% palmitic acid, 0.1% 13-hydroxy-9,11-octadecadieonic acid and 0.4% cerebrosides.

BRIEF DESCRIPTION OF THE DRAWINGS

Embodiments of the invention will be shown in relation to the drawings in which the following is shown.

DETAILED DESCRIPTION

Figure 1:
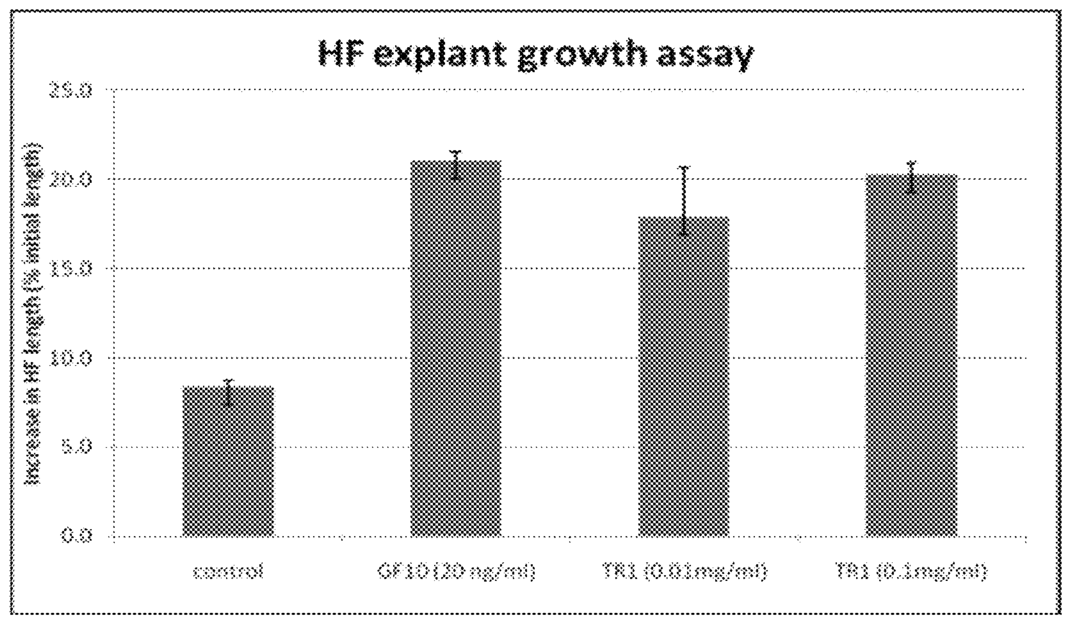
FIG. 1: Total aqueous extract of *F. benghalensis* aerial roots (TR1) increases hair follicle explant growth at 0.01 mg/ml and 0.1 mg/ml.

The present application relates to natural product extracts, fractions and compounds from *Ficus* plants useful for increasing hair growth and decreasing hair loss.

The term "*Ficus*" refers to any species of the *Ficus* genus. The term "*Ficus* having an aerial root" refers to plants of the species *Ficus* with at least one aerial root. One example of such a plant is *Ficus* benghalensis. Other *Ficus* plants that may grow aerial roots include, but are not limited to, *Ficus benjamina, Ficus microcarpa, Ficus citrifolia* and *Ficus retusa.*

The term "aerial root" refers to a root growing above the ground and exposed to air. Aerial roots grow rapidly due to the presence of root meristem cells. The term "aerial root tip" refers to the end of the aerial root, typically located on the portion of the aerial root furthest from the trunk of the tree depending on the direction of growth. The term "aerial root portion" refers to any portion of an aerial root. Optionally, the aerial root portion comprises the tip of an aerial root. Optionally, the aerial root portion comprises the outer 5 to 15 centimeters of an aerial root including the tip. Optionally, the aerial root portion comprises the outer 10 centimeters or the outer 5 centimeters or less of an aerial root including the tip:

The term "crude extract" refers to a concentrated preparation of vegetation that has not been subjected to any solvent extractions. For example, a crude extract can consist of vegetation that has been dried and processed into a powder form. The terms "extract", "fraction" or "sub-fraction" refer to a concentrated preparation of plant material that has been obtained by removing active constituents with a suitable solvent. Numerous extracts, fractions and/or sub-fractions can be obtained from a single crude extract. In one embodiment of the invention, the "crude extract" is a total aqueous extract or a water extract. Optionally, the total aqueous extract is obtained by pulverizing the aerial root of a Ficus and boiling the resulting powder. A "n-hexane fraction" is a fraction eluted with n-hexane. A "dichloromethane fraction" is a fraction eluted with dichloromethane. An "ethyl acetate fraction" is a fraction eluted with ethyl acetate. A "methanol fraction" is a fraction eluted with methanol. A "water fraction" is a fraction eluted with water.

The term "sub-fraction" refers to a fraction obtained during the sub-fractionation of a fraction of a crude extract. Sub-fractionation is optionally performed by chromatography such as high performance liquid chromatography (HPLC) or vacuum assisted liquid chromatography or any other method known in the art. In another embodiment, sub-fractionation is performed through solvent partitioning. A sub-fraction may be sub-fractionated into further sub-fractions.

The terms "active extract", "active fraction" or "active sub-fraction" relate to an extract, fraction or sub-fraction that is alternatively at least 5%, 10%, 20%, 50% or more than 100% more active per unit weight than its parent fraction, as measured by a hair follicle explant growth assay, a hair follicle explant viability assay or any other assay designed to measure hair-growth promoting activity. In one embodiment, a "hair follicle explant growth assay" is an assay that analyzes the growth of explant hair follicles in vitro. In another embodiment, a "hair follicle explant viability assay" is an assay that analyzes the viability of explant hair follicles in vitro.

In another embodiment, an "active extract", "active fraction" or "active sub-fraction" is an extract, fraction or sub-fraction that is alternatively at least 5%, 10%, 20%, 50% or more than 100% more active per unit weight than the crude extract from which it was originally derived, as measured by a hair follicle explant growth assay, a hair follicle explant viability assay or any other assay designed to measure hair-growth promoting activity.

In another embodiment, an "active extract", "active fraction" or "active sub-fraction" is an extract, fraction or sub-fraction that contains at least 5%, 10%, 20%, 50%, 75% or 100% of active compound(s). An active compound is a compound that promotes hair growth as measured by a hair follicle explant growth assay, a hair follicle explant viability assay or any other assay designed to measure hair-growth promoting activity.

The terms "increases hair growth" and "promotes hair growth" include, but are not limited to, activity that increases the number of hairs on a mammal, maintains the number of hairs in a given area of scalp on a mammal that would otherwise experience net hair loss, grows hair on a mammal, re-grows hair on a mammal, increases the length or thickness of hair on a mammal, improves the health of hair on a mammal, treats baldness (for example, male pattern baldness, female pattern baldness, genetic alopecia) and/or increases hair follicle density. The term "increasing hair growth" includes activity that stimulates growth of a single hair in a follicle or growth of a group of hairs in hair follicles in specified area of epidermis. Increasing hair growth optionally occurs, for example, by increasing the number of hairs present in an area of epidermis of a mammal or maintaining the number of hairs present in an area of epidermis of a mammal that would otherwise experience net hair loss (optionally measured per square cm). Increasing hair growth optionally causes growth of a new hair in a follicle (e.g. after a hair has fallen out) or increases rate of growth of an existing hair (length and/or width) of a hair in a follicle on a mammal. Increasing hair growth optionally increases hair length. Increasing hair growth prevents (reduces) and/or treats baldness and/or balding. It optionally has other effects such as increasing hair follicle density in an area and/or the appearance of thickness of hair in an area. Increasing hair growth optionally also improves the health of hair and hair follicles on a mammal. Typically the increase in the foregoing parameters that are quantifiable will be at least: 5%, 10%, 20%, 50%, 100% or 150% compared to untreated hair follicles (or epidermis) that do not experience the present methods and compositions that increase hair growth. These percentage increases are optionally measured in a single hair or single hair follicle (e.g. rate of increased growth, increase in length or thickness per day) or in a plurality of hairs or hair follicles in a specified area (e.g. increase in number of hairs per square cm or in length of hairs growing per square cm).

The term "increasing hair growth" optionally refers to increasing the viability of hair follicles in vivo or in vitro. The term "increasing hair growth" also optionally refers to increasing the viability of an isolated hair follicle, i.e. an isolated hair follicle in culture (in vitro). Increasing the viability of hair follicles in vitro can be measured through a hair follicle explant growth assay, a hair follicle explant viability assay or any other method known in the art. Typically the increase in the foregoing parameters will be at least: 5%, 10%, 20%, 50%, 100% or 150% compared to untreated hair follicles that do not experience the present methods and compositions that increase hair growth.

The term "decreases hair loss" includes, but is not limited to, activity that maintains the number of hairs or hair follicles on a mammal that would otherwise experience net hair loss (optionally measured as the number of hairs or hair follicles measured per square cm), reduces the rate of balding and/or reduces the rate of hair follicle miniaturization. Decreasing hair loss optionally decreases the rate of hair loss, hair follicle loss and/or hair follicle miniaturization by at least 5%, 10%, 20%, 50%, 100% or 150% compared to untreated hair follicles (or epidermis) that do not experience the present methods and compositions that decrease hair loss. These percentage increases are optionally measured in a single hair or single hair follicle or in a plurality of hairs or hair follicles in a specified area.

The term "increases cell viability" refers to increasing the viability of cells, whether in vivo or in vitro. The term "increases isolated cell viability" refers to increasing the viability of isolated cells in culture (in vitro). The term can refer to increasing the growth of one or more hair follicle cells such as dermal papilla cells, outer root sheath cells, epidermal stem cells, dermal sheath cells or epidermal matrix cells. In one example, cell viability is determined by incubating cells with methanethiosulfonate (MTS) reagents and measuring optical density (OD) 490 nm spectrophotometrically. Optionally, increased cell viability is indicated by an increase in the percent survival of treated cells versus non-treated cells. Typically, the increase in cell viability will be quantifiable, for example, 110%, 120%, 150%, 200% or 500% viability compared to a control. The term "increases hair follicle viability" refers to increasing the viability of hair follicles, whether in vivo or in vitro. The term "increases isolated hair follicle viability" refers to increasing the viability of isolated hair follicles in culture (in vitro). Optionally, increased hair follicle viability is indicated by an increase in the percent survival of treated hair follicles versus non-treated hair follicles. Typically, the increase in hair follicle viability will be quantifiable, for example, 110%, 120%, 150%, 200% or 500% viability compared to a control. Hair follicle viability is assessed by any method known in the art to quantify hair follicle viability, optionally a hair follicle explant assay.

The term "rejuvenating skin" includes increasing the health of skin, improving the appearance of skin, decreasing signs of skin aging, for example, decreasing the presence or appearance of wrinkles, fine lines or age spots or increasing the viability of skin cells. Typically the increase or decrease in the foregoing parameters will be at least: 5%, 10%, 20%, 50%, 100% or 150% compared to untreated skin which does not experience the present methods and compositions that rejuvenate skin.

*Ficus benghalensis* is also known as Bengal fig, Indian fig, East Indian fig, Banyan, Bargad or Bod (Kala et al., 2004). It is a species of *Ficus* that is typically found in high concentrations in Bangladesh, India and Sri Lanka, though it can be cultivated in other places. *F. benghalensis* produces aerial roots, which grow downwards as slender vine. Once these roots reach the ground, they take root and grow into woody trunks that can become indistinguishable from the main trunk.

The aerial roots of *F. benghalensis* typically grow a few centimeters per day. Optionally the aerial roots grow at least 0.5 cm per day in length in soil or hydroponic conditions that support *Ficus* growth. The growth and differentiation of meristem cells or plant stem cells is supported by various growth promoting factors in these areas (Tucker and Laux, 2007). Without being bound by theory, the longevity and fast incessant growth of *F. benghalensis* aerial roots may reflect the presence of such stem cell mobilizing factors.

In one aspect of the invention, aerial roots of a *Ficus* plant are dried and powdered to obtain a crude extract. The method of extraction optionally includes extracting a portion of the aerial root. The portion of the aerial root extracted can be the end portion of the aerial root that is actively growing in length. The method of extraction optionally includes extracting the outer 5 to 15 centimeters of the root length (the end of the root tip and the 5 to 15 centimeters proximate to the end), or optionally the outer 10 centimeters or outer 5 centimeters, or less of the root length (the end of the root tip and the 5 or 10 centimeters proximate to the end). The method of extracting also optionally includes extracting a portion of the *Ficus* aerial root that has grown in length over the 15 day period prior to cutting or any time period therein (for example, the 2 day period prior to cutting, the 5 day period prior to cutting or the 10 day period prior to cutting).

In one embodiment of the invention, fractions of the crude extract are extracted by methods known in the art. Optionally, the crude extract is fractionated by performing a Soxhlet extraction with a series of solvents. In one aspect of the invention, the crude extract is fractioned with 250 to 750 ml of each solvent. In another aspect of the invention, the crude extract is fractionated with approximately 500 ml of each solvent per 100 g of crude extract. The solvents can include, but are not limited to, n-hexane, dichloromethane, ethyl acetate, methanol and water. The extraction of the various fractions can occur in the following sequence: n-hexane extraction, dichloromethane extraction, ethyl acetate extraction, methanol extraction and water extraction. Other types of extractions and solvents will be readily apparent.

The crude extract can be fractionated with a solvent with a dielectric constant of 1.1 to 4.0, typically 1.5 to 2.5. Most typically, the crude extract is fractionated with n-hexane, which has a dielectric constant of 1.9. The crude extract can also be fractionated with solvents having similar physico-chemical properties to those of n-hexane. Optionally, the method of extraction includes fractionating with hexane or any of its isomers.

The crude extract or any one of the fractions of the crude extract of aerial roots of a *Ficus* plant can be used to increase hair growth or decrease hair loss. In particular, the n-hexane extracted fraction, the ethyl acetate extracted fraction or the water extracted fraction are useful to increase hair growth or decrease hair loss. The extracts and fractions directly useful to increase hair growth or decrease hair loss can be formulated in a composition. In one embodiment, the composition comprises the n-hexane fraction, the dichloromethane fraction, the ethyl acetate fraction and/or the methanol fraction. In another embodiment, the composition consists of, or consists essentially of the n-hexane fraction, the dichloromethane fraction, the ethyl acetate fraction and/or the methanol fraction.

In another aspect of the invention, the n-hexane fraction of the crude *Ficus* extract (TR2) is sub-fractioned into a number of sub-fractions. The sub-fractionation is readily performed by chromatography, such as high performance liquid chromatography, or any other separation method known in the art.

The invention provides a sub-fraction of the n-hexane fraction of the crude *Ficus* extract (TR2) containing cerebrosides. Cerebrosides are glycosphingolipids that consist of a ceramide (composed of sphingosine and a fatty acid) with a single sugar residue at the 1-hydroxyl moiety.

The invention also provides a sub-fraction containing terpenes, saturated fatty acids and unsaturated fatty acids. Terpenes are a large class of hydrocarbons produced primarily by plants. Terpenes are derived biosynthetically from units of isoprene. Isoprene has the molecular formula $C_5H_8$.

The invention also provides a sub-fraction comprising psoralen. Psoralen is the parent compound in a family of natural products known as furocoumarins.

The invention further provides a sub-fraction containing polar disaccharide and a sub-fraction containing coumarins. Coumarins are a group of compounds found in many plants. Psoralen and its derivatives belong to the coumarin class of compounds.

In another aspect of the invention, the n-hexane fraction of the crude *Ficus* extract is sub-fractioned through solvent partitioning. In a further aspect of the invention, the n-hexane fraction of the crude *Ficus* extract is partitioned with chloroform to give a chloroform soluble fraction.

In yet another aspect of the invention, the chloroform soluble fraction is further sub-fractionated into a number of sub-fractions. In a preferred embodiment, the chloroform soluble fraction is further sub-fractionated using preparative VLC (silica gel) fractionation. The further sub-fractions obtained from the preparative VLC (silica gel) fractionation may be further fractionated again by chromatography, such as high performance liquid chromatography, or any other method known in the art.

The invention provides a further sub-fraction of the choloroform soluble fraction containing any one of the following compounds: saturated fatty acids, psoralen, 5-methoxypsoralen, psoralen analogues, cerebrosides, glucosylceramide, terpenes, octadecenoic acids, betulinic acid, betulonic acid, palmitic acid, 13-hydroxy-9,11-octadecadienoic acid and 18-hydroxy-9-octadecenoic acid, saturated ester waxes (for example, hexacosyl tetracosanoate, hexacosyl hexacosanoate, hexacosyl tetracosanoate and hexacosyl docosanoate), cycloartenol, α-amyrin, lupeol, stigmasterol, β-sitosterol and 5-methoxypsoralen.

The invention also provides a sub-fraction comprising the following compounds: lupeol, cycloartenol, α-amyrin, saturated ester wax, 5-methoxypsoralen, stigmasterol, β-sitosterol, betulinic acid, betulonic acid, palmitic acid, 13-hydroxy-9,11-octadecadieonic acid and cerebrosides. Optionally, the sub-fraction comprises at least 0.3% by weight lupeol, 0.4% by weight cycloartenol, 0.4% by weight α-amyrin, 0.7% by weight saturated ester wax, 1.2% by weight 5-methoxypsoralen, 5% by weight stigmasterol and β-sitosterol, 0.3% by weight betulinic acid, 0.8% by weight betulonic acid, 0.46% by weight palmitic acid, 0.1% by weight 13-hydroxy-9,11-octadecadieonic acid and 0.4% by weight cerebrosides.

The invention also provides a plurality of sub-fractions of the n-hexane fraction, wherein the plurality of sub-fractions are obtained by partitioning the n-hexane fraction with a solvent, optionally chloroform, loading the solvent partitioned fraction into a chromatography column and eluting the solvent partitioned fraction through sequential elution to obtain a plurality of sub-fractions. Optionally, the solvent partitioned fraction is eluted using solvent mixtures ranging from 100% hexane to 100% chloroform to 100% methanol. In one embodiment, the chromatography is vacuum assisted liquid chromatography. In one specific embodiment, the plurality of sub-fractions are the 30 sub-fractions listed in Table 9 (also known as TR3). The invention also provides a composition comprising the plurality of sub-fractions. In a preferred embodiment, the composition does not contain a sub-fraction eluted at 97% chloroform: 3% methanol. In another embodiment, the composition does not contain a sub-fraction comprising unsaturated fatty acids, optionally 85-90% unsaturated fatty acids. In yet another embodiment, the composition does not include a sub-fraction that decreases the viability, optionally by at least 5%, at least 10%, at least 20%, at least 30% or at least 50%, of explant hair follicles at 1 μg/ml.

In another embodiment, the invention provides a composition comprising the chloroform partititioned fraction wherein a sub-fraction eluted at 97% chloroform:3% methanol has been removed. Optionally, the removed sub-fraction comprises unsaturated fatty acids, optionally 85-90% unsaturated fatty acids. In yet another embodiment, the removed sub-fraction decreases the viability, optionally by at least 5%, at least 10%, at least 20%, at least 30% or at least 50%, of explant hair follicles at 1 μg/ml.

The invention also relates to the use of a composition comprising or consisting the plurality of sub-fractions to increase hair growth or to decrease hair loss. The composition may comprise or consist of the 30 sub-fractions listed in Table 9 (also known as TR3) in a suitable carrier. In one embodiment, the carrier is a cosmetic carrier. In another embodiment, the composition comprises the following compounds: lupeol, cycloartenol, alpha-amyrin, saturated ester wax, 5-methoxypsoralen, stigmasterol, β-sitosterol, betulinic acid, betulonic acid, palmitic acid, 13-hydroxy-9,11-octadecadieonic acid and cerebrosides. In another embodiment, the composition consists essentially of the following compounds: lupeol, cycloartenol, α-amyrin, saturated ester wax, 5-methoxypsoralen; stigmasterol, β-sitosterol, betulinic acid, betulonic acid, palmitic acid, 13-hydroxy-9,11-octadecadieonic acid and cerebrosides. Optionally, the compounds are present in the composition in at least the percentage amounts listed in Table 8.

The invention also relates to the use of a composition comprising an extract, fraction or sub-fraction of *Ficus* which has activity to increase hair growth or decrease hair loss, singly or together, to increase hair growth or decrease hair loss. The invention further relates to the use of a composition consisting of, or consisting essentially of an extract, fraction or sub-fraction of *Ficus* which has activity to increase hair growth or decrease hair loss, singly or together, to increase hair growth or decrease hair loss.

In addition, the invention relates to the use, singly and together in any combination, of a composition comprising a compound or class of compound described above which has activity to increase hair growth or decrease hair loss to increase hair growth or decrease hair loss. The invention further relates to the use, singly and together in any combination, of a composition consisting of, or consisting essentially of a compounds or class of compound described above which has activity to increase hair growth or decrease hair loss to increase hair growth or decrease hair loss.

The invention further relates the use of a composition comprising, consisting or, or consisting essentially of an extract, fraction, sub-fraction or compound described above which has activity to increase hair growth or decrease hair loss, alone or in combination, to generate new hair on a subject. In one aspect of the invention, a new hair is generated from a pre-existing follicle. In another aspect of the invention, a follicle giving rise to a new hair is generated. The generation of new hair may comprise increasing the density of individual hairs and/or hair follicles within a specified area of a patient's scalp. Optionally, hair density is increased by 5%, 10%, 20%, 50% or more than 100%. In one embodiment of the invention, a composition comprising, consisting of, or consisting essentially of an extract, fraction, sub-fraction or compound described above which has activity to increase hair growth or decrease hair loss, alone or in combination, is topically applied to a subject for use in generating new hair.

The invention further relates the use of a composition comprising, consisting or, or consisting essentially of any of the extracts, fractions, sub-fractions and compounds described above, alone or in combination, to thicken a hair shaft on a subject. Optionally, the diameter of a thickened hair shaft is increased by 5%, 10%, 20%, 50% or more than 100% following treatment with a composition of the invention. Optionally, the diameter of a thickened hair shaft is increased by at least 10-100 μm, optionally 20-50 μm.

The invention further relates the use of a composition comprising, consisting or, or consisting essentially of an extract, fraction, sub-fraction or compound described above, alone or in combination, to increase the rate of hair growth on a subject. Optionally, the rate is increased by 5%, 10%, 20%, 50% or more than 100% following treatment with a composition of the invention.

The invention further relates the use of a composition comprising, consisting or, or consisting essentially an extract, fraction, sub-fraction or compound described above which has activity to increase hair growth or decrease hair loss, alone or in combination, to increase the longitudinal hair growth of a subject. Optionally, longitudinal hair growth is increased by 5%, 10%, 20%, 50% or more than 100% following treatment with a composition of the invention.

The invention also relates to the use of a composition comprising, consisting or, or consisting essentially of an extract, fraction, sub-fraction or compound described above which has activity to increase hair growth or decrease hair loss, alone or in combination, to increase the viability of hair follicles in vitro.

The invention also relates to the use of a composition comprising, consisting or, or consisting essentially of an extract, fraction, sub-fraction or compound described above which has activity to increase hair growth or decrease hair loss, alone or in combination, to increase the viability of hair follicle cells, for example, outer root sheath cells, epidermal stem cells, dermal papilla cells, dermal sheath cells and epidermal matrix cells.

In one embodiment, the compositions of the invention are topical compositions that are typically applied to the scalp or skin by spraying or coating. The compositions for external dermal applications can be formulated as liquids, milky lotions, gels, creams, aerosols, sprays, powders, cosmetics or rinses. There are no limitations to the method by which the compositions can be applied. For example, 1 to 5 ml of the compositions could be applied to scalp or skin surface areas 1 to 3 times per day.

Optionally, the compositions of the invention are formulated in a suitable dermal penetration carrier or pharmaceutically acceptable carrier. Optionally, the carrier is a cosmetic carrier. The carrier may contain antioxidants, vitamins, preservatives, anti-microbials, colorants, moisturizers, thickeners and preservatives that do not interfere with the desired effects of the present invention.

Suitable pharmaceutically acceptable carriers include essentially chemically inert and nontoxic compositions that do not interfere with the effectiveness of the biological activity of the pharmaceutical or cosmetic composition. Examples of suitable pharmaceutical or cosmetic carriers include, but are not limited to, water, saline solutions, glycerol solutions, ethanol, N-(1(2,3-dioleyloxy)propyl)N,N,N-trimethylammonium chloride (DOTMA), diolesylphosphotidyl-ethanolamine (DOPE), and liposomes. Such compositions should contain a therapeutically effective amount of the compound(s), together with a suitable amount of carrier so as to provide the form for administration to the subject.

In one embodiment of the invention, the carrier is WE-basic medium plus 25% glycerol. In another embodiment, the carrier is a basic oily carrier, optionally a basic oily carrier comprising the following ingredients: dicapryl ether, octyldodecanol, oryza sativa bran oil, prunus amygdalus dulcis oil, lecithin, tocopherol, ascorbyl palmitate and citric acid.

The compositions of the invention optionally contain between 0.0001% to 100% by weight of the active extract, fraction, sub-fraction and/or compound. Optionally, the compositions of the invention contain between 0.001% and 1% by weight of the active extract, fraction, sub-fraction and/or compound. Optionally, the compositions of the invention contain between 1 μg/ml to 0.1 mg/ml, optionally 10 μg/ml to 100, 150, 200 or 250 μg/ml, of the active extract, fraction, sub-fraction and/or compound.

In one particular embodiment, the invention relates to a composition comprising 0.1 μg/ml to 250 μg/ml TR1 (total aqueous extract of *F. benghalensis*), optionally 0.1 μg/ml to 100, 150, 200 or 250 μg/ml TR1, preferably 1 μg/ml to 100 μg/ml TR1, preferably 10 μg/ml to 50 μg/ml TR1. Typically, a TR1 composition is administered to a subject in order to increase hair growth or decrease hair loss at a dosage of 1 μg to 200 μg TR1 per day, preferably 20 μg to 100 μg per day.

In another particular embodiment, the invention relates to a composition comprising 0.1 μg/ml to 250 μg/ml TR2 (hexane extracted fraction of *F. benghalensis*), optionally 0.1 μg/ml to 100, 150, 200 or 250 μg/ml TR2, preferably 1 μg/ml to 100 μg/ml TR2, preferably 10 μg/ml to 50 μg/ml TR2. Typically, a TR2 composition is administered to a subject in order to increase hair growth or decrease hair loss at a dosage of 1 μg to 200 μg TR2 per day, preferably 20 μg to 100 μg per day.

In another particular embodiment, the invention relates to a composition comprising 0.1 μg/ml to 250 μg/ml TR3, optionally 0.1 μg/ml to 100, 150, 200 or 250 μg/ml TR3, preferably 1 μg/ml to 100 μg/ml TR3, preferably 10 μg/ml to 50 μg/ml TR3. Typically, a TR3 composition is administered to a subject in order to increase hair growth or decrease hair loss at a dosage of 1 μg to 200 μg TR3 per day, preferably 20 μg to 100 μg per day.

Optionally, the compositions of the invention are administered subcutaneously, subdermally, intramuscularly or intravenously.

The dosage of the compositions vary according to the specific form of the external application, age and the type and degree of hair loss. FIG. 20 depicts the seven classes of hair loss as defined by the Norwood scale of hair loss. Optionally, the compositions of the invention are administered to subjects with hair loss as classified by the Norwood scale as class 2 (mild hair loss), class 3 (mild to moderate hair loss), class 4 (moderate hair loss), class 5 (moderate to large hair loss), class 6 (large hair loss) or class 7 (complete hair loss). Optionally, the compositions of the invention are administered to subjects with no hair loss (class 1) in order to prevent future hair loss.

In one aspect of the invention, the compositions are used for treating hair loss or baldness. Optionally, the compositions are also used for preventing or reducing hair loss or baldness (e.g. stopping or slowing hair loss progression). Since the compositions are natural products with no known side effects, they are also useful for individuals with no signs of hair loss at all who wish to use the product to prevent or reduce risk of hair thinning or hair loss on a prophylactic basis. The compositions are therefore useful by themselves or as additives to products such as shampoo, conditioner, mousses, gels or creams as well as other cosmetics and drugs (typically over the counter drugs). These products are topically administered according to methods described herein.

In another aspect of the invention, the compositions are used conjunction with hair transplant surgery. Optionally, the compositions are administered to a patient prior to surgery, during surgery, or following surgery. The invention therefore relates to a method of transplanting hair in a subject by implanting a hair follicle in the subject and contacting the hair follicle with a composition described herein. The hair follicle of the subject can be contacted with the composition prior to, during, or after transplantation. The follicle transplant is typically made onto a human scalp and the compositions are optionally used for at least one week, four weeks or at least 52 weeks.

In one embodiment of the invention, the compositions are used to promote the viability of cells derived from hair follicles. Cells derived from hair follicles include, but are not limited to, dermal papilla cells, outer root sheath cells, dermal sheath cells and epidermal matrix cells. In one aspect of the invention, the compositions are added to cell culture medium to increase the viability of hair follicle cells in vitro. In another embodiment of the invention, the compositions are used to promote the viability of skin cells.

In another embodiment of the invention, the compositions are used to promote the viability of explant hair follicles in vitro. In another aspect, the compositions are used to increase the length of explant hair follicles in vitro. The invention therefore relates to a method of increasing the length or viability of hair follicles in vitro by contacting the hair follicle with a composition described herein. Optionally, the invention relates to a method of increasing the length or viability of hair follicles in vitro by maintaining the hair follicles in media comprising a composition described herein.

EXAMPLES

Embodiments of the present invention will be illustrated in a non-limiting way by reference to the examples below.

Example 1

Total Aqueous Extracts of *F. benghalensis* Aerial Root Tips

Sample Collection

*F. benghalensis* var. *benghalensis* (Banyan) trees grown in rural non-residential area far from industries and heavy traffic roads were selected. Samples were obtained from at least 5 trees located at least 100 meters apart. The trees were confirmed to be species *F. benghalensis* at a certified botanic centre. Ten centimeter long intact aerial root tips were collected from longer prop roots (roots originating from higher branches but yet reaching the ground). The collected intact root tips from each tree separately weighed at least 500 grams.

Sterilization

Aerial root tips of each *F. benghalensis* tree were rinsed with sterile double distilled water, immersed in 70% aqueous ethanol for 60 seconds, rinsed three times with sterile double distilled water three times, surface sterilized with a 5% (w/v) NaOCl solution for 10 minutes and rinsed again three times with sterile double-distilled water (Sokmen et al. 2004; Liqing Z. et al. 2005).

Total Aqueous Extracts (Crude Extracts)

Sterilized root tips were shade-dried for 5-7 days and pulverized using a pestle and mortar. The pulverized parts may be stored in cellophane bags at room temperature. 100 g of the root tip powder was subjected to exhaustive Soxhlet extraction in 500 ml of distilled water for 72 hours. Each extract was concentrated in a water bath until a constant color residue was obtained (Garba et al. 2006). The extract was further lyophilized and stored in a tightly capped container in the freezer (Channabasavaraj et al. 2008).

Preparation of Stock and Test Solutions

Stock solution of the aqueous extract was prepared by dissolving the lyophilized powder in $Ca^{2+}$- and $Mg^{2+}$-free phosphate buffered saline (PBS). The stock solution had a final concentration of 250 mg/ml and was stored at 4° C. Aqueous extracts for the required treatment regimens were freshly prepared by serially diluting the stock solution with cell culture medium (Garba et al. 2006).

Example 2

*F. benghalensis* Extract Increases Hair Follicle Explant Growth

Hair follicles were obtained through standard surgical procedures and placed in Petri dishes containing 5× antibiotic/PBS for 20 minutes at room temperature. After washing in saline or phosphate buffered saline, the hair follicles were transferred to Williams' E growth media (WE; Invitrogen) and placed inside the incubator until ready for use. The follicles were cut below the epidermis, leaving an intact hair follicle bulb with dermal papilla, hair fiber, and outer root sheath.

Growth of the follicles was measured with Zeiss DV4 Stereo Microscope equipped with a reticle. Whole hair follicle length was measured before treatment and after incubating under the defined conditions for 7 to 8 days at 37° C., 5% $CO_2$.

FIG. 1 shows growth of hair follicles as a percentage of the initial length for each treatment. Each experimental point represents a summary of 3 to 4 individual experiments in different patients. Data are the mean±SEM (SEM, standard error of mean) of at least 4 individual patients. The media only control consists of WE substituted with L-glutamine (2 mmol/L), hydrocortisone (10 ng/ml) and antibiotic solution 1× (100 units/ml penicillin, 100 μg/ml streptomycin and 0.25 μg/ml amphotericin). The "Growth factor 10 mixture" contains IGF-I, FGF-2, FGF-10, PDGF-AA, Wnt-3A, Noggin, Ephrin-A3, SHH, BMP-6 each at 20 ng/ml, and hypoxanthine at 2 μmol/L (2 μM) final concentration. TR1 refers to the total aqueous extract of *F. benghalensis*. The TR1 extract promoted hair follicle (HF) explant growth at concentrations of 0.01 mg/ml and 0.1 mg/ml.

Figure 2:
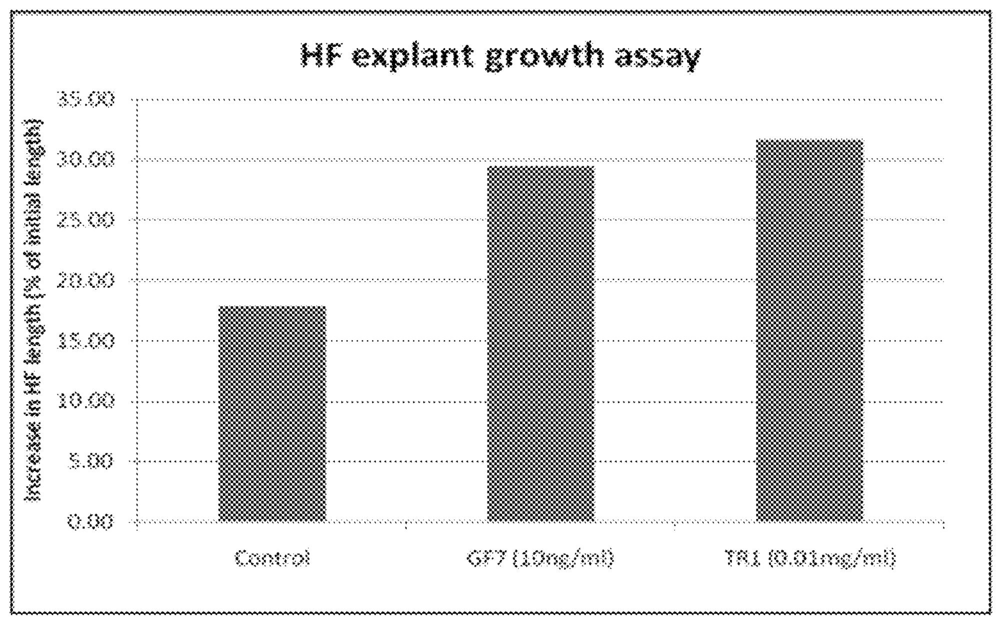
FIG. 2: Total aqueous extract of *F. benghalensis* aerial roots (TR1) increases hair follicle explant growth at 0.01 mg/ml.

FIG. 2 shows a hair follicle explant growth assay performed as described for FIG. 1. The GF7 treatment consists of 7 growth factors (IGF-1, FGF-2, PDGF-AA, Wnt-3a, Noggin, BMP-6; at 10 ng/ml; hypoxanthine at 1 μmol/L). TR1 at 0.01 mg/ml induced more growth compared to the control as well as the GF7 treatment.

Example 3

*F. benghalensis* Extract Promotes Dermal Papilla Cell Viability

Figure 3:
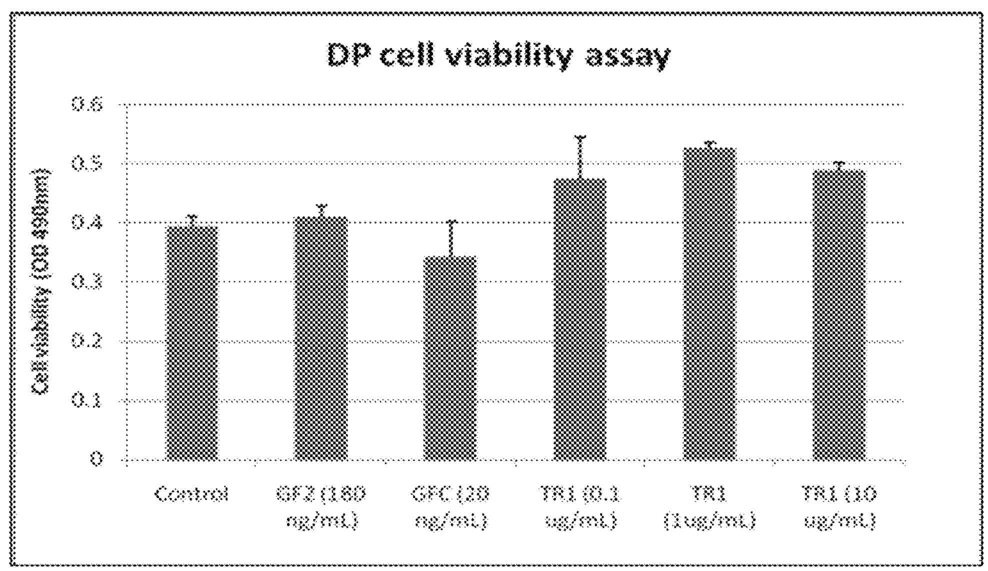
FIG. 3: Total aqueous extract of *F. benghalensis* aerial roots (TR1) increases dermal papilla cell viability.

Dermal papilla (DP) cells were isolated from hair follicles. The cells were plated and treated with the total aqueous extract of *F. benghalensis* (TR1) for different durations by incubating at 37° C. with 5% CO2. To assess cell viability after treatment, a MTS (methanethiosulfonate) viability assay was performed: 5 μl MTS reagents (Promega, WI) were added per 100 μl cells. Cells were incubated further for 2.5 hrs at the end of which OD at 490 nm was measured spectrophotometrically. The color developed at this wavelength is directly proportional to the viability of cells in the medium. As shown in FIG. 3, increased DP cell viability was observed from 0.1 to 10 μg/ml TR1.

Example 4

Topical Application of Total *F. benghalensis* Extract Increases Hair Density A patient's scalp was mapped to 4 specific bald zones: 1) 1R+IL (Zone 1 Right and Left), 2) 1M (Zone 1 Middle), 3)

Figure 4A:
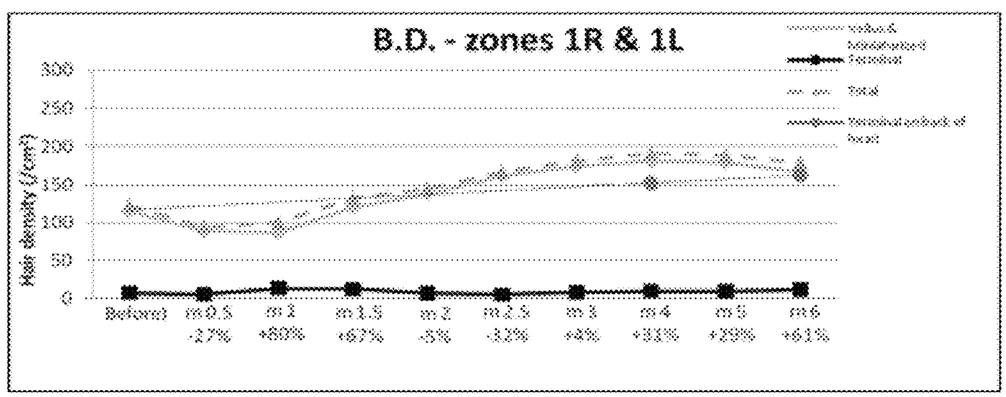
FIG. 4A-D: A patient (B.D.) treated for 6 months with a topical formulation containing total aqueous extract of *F. benghalensis* aerial roots (TR1) shows an approximately 146% increase in terminal hair density averaged over all zones of the scalp. The scalp zone referenced in each chart is also indicated (see also FIG. 4G).
Figure 4A:
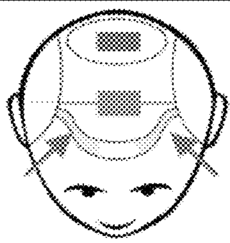
Figure 4B:
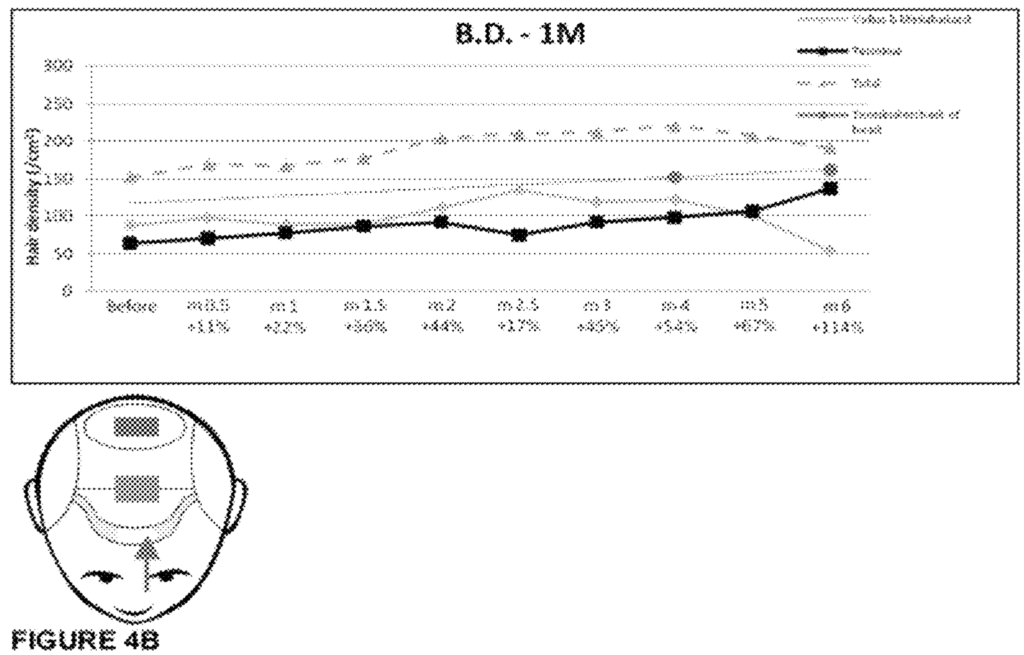
Figure 4C:
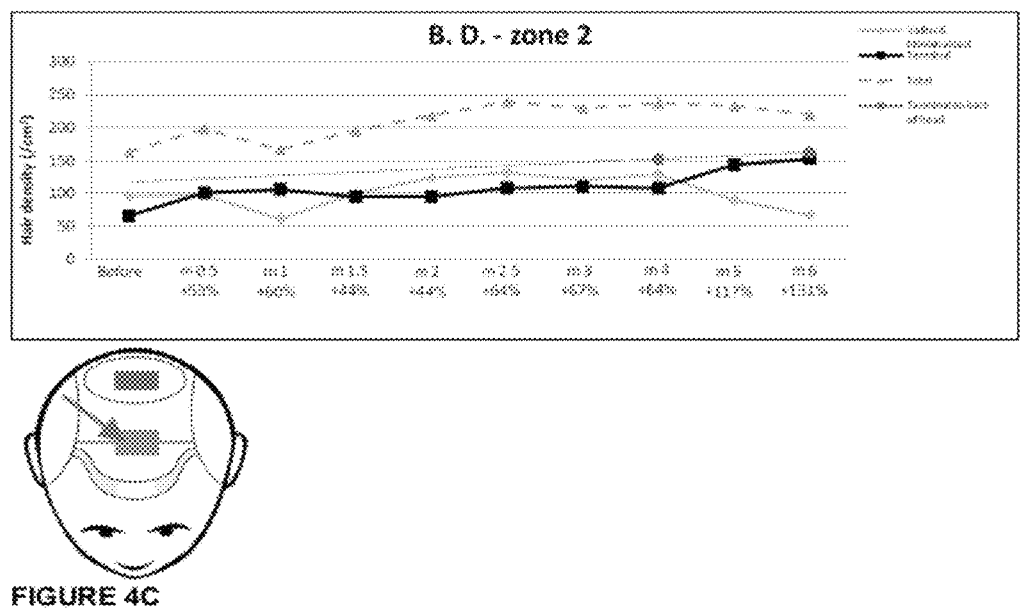
Figure 4D:
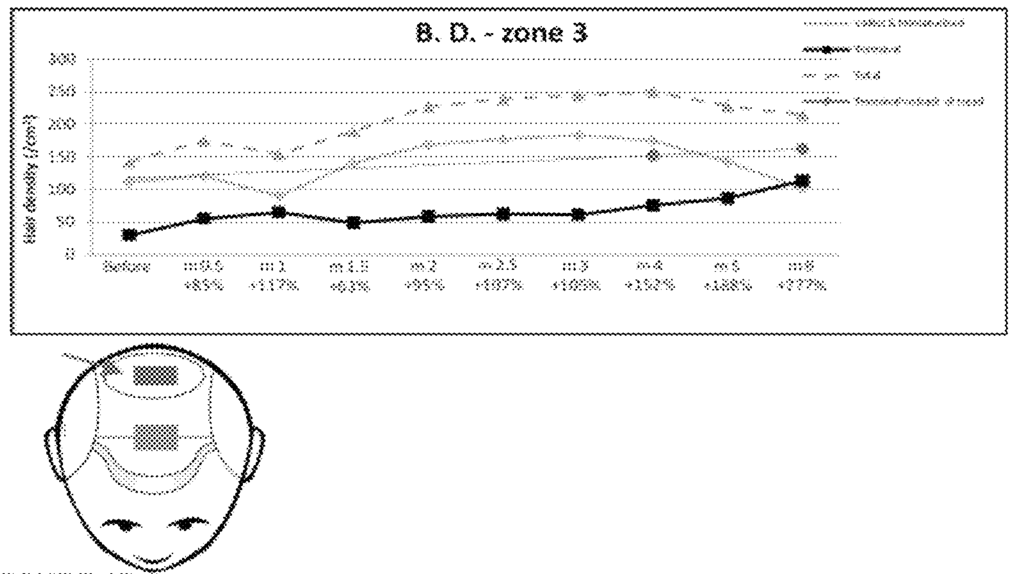
Figure 4E:
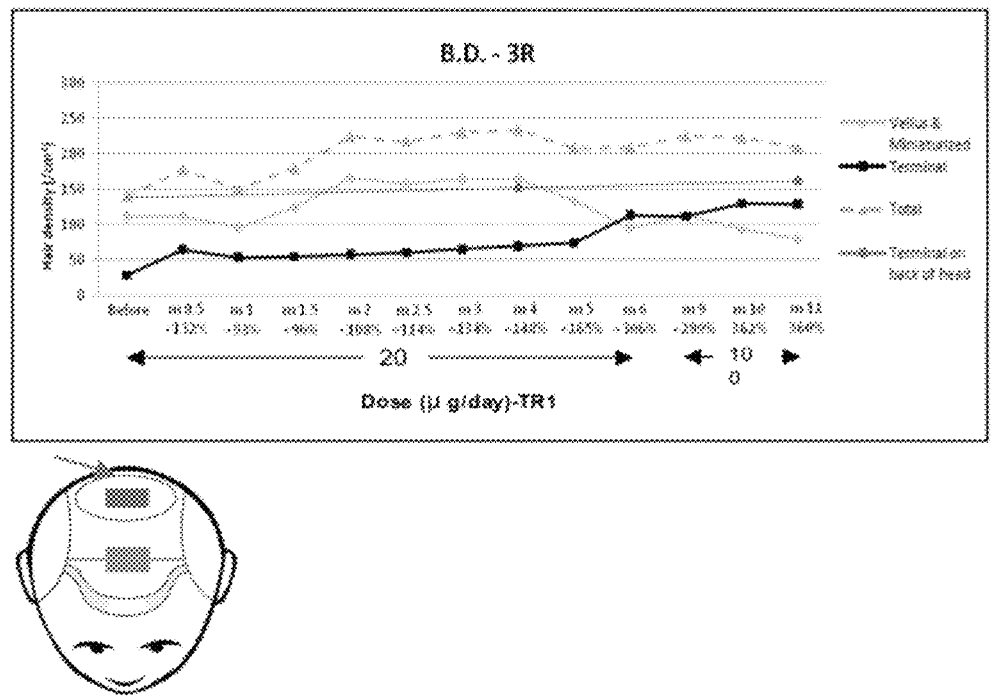
FIG. 4E: A patient (B.D.) treated for 8 months with a topical formulation containing total aqueous extract of *F. benghalensis* aerial roots (20 μg/day TR1 for 6 months and 100 μg/day TR1 for months 9 to 11) shows an increase in terminal hair density and a corresponding decrease in vellus and miniaturized hair density. The formulation was applied to zone 3-Right (3R) of the patient's scalp. Extract dosage is depicted in the horizontal axis in micrograms per day. Cumulative increase in terminal hair density (black solid rectangles) as a % of before treatment is also shown; treatment duration in months (m) represented in the x-axis.
Figure 4F:
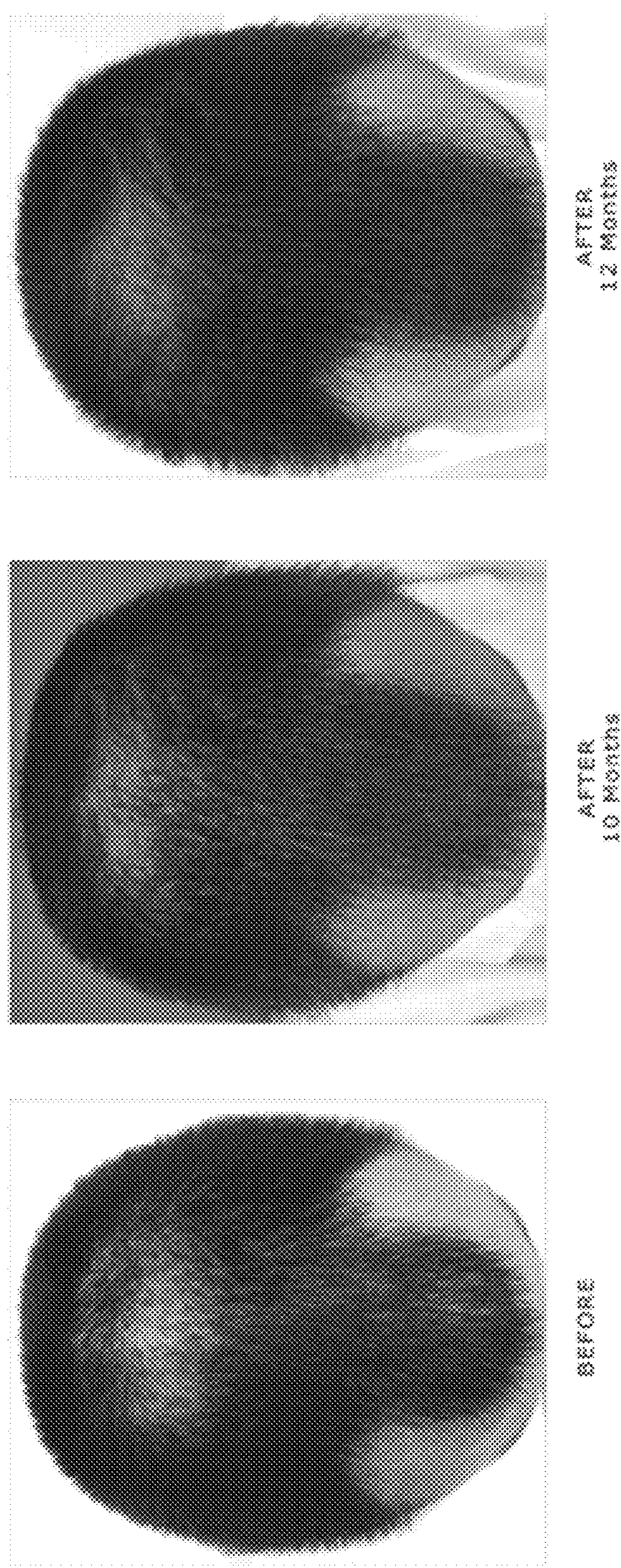
FIG. 4F: A patient (B.D.) treated in scalp zone 3R with a topical formulation containing total aqueous extract of *F. benghalensis* aerial roots (TR1) and TR3 shows increased hair growth. The patient was treated with 20 μg/day of the TR1 extract up to month 6, had no treatment from the $6^{th}$ month to the $9^{th}$ month and was treated with 100 μg/day of TR1 from the $9^{th}$ month to the $10^{th}$ month followed by 26 μg/day of TR3 from the $10^{th}$ to $12^{th}$ month.
Figure 4G:
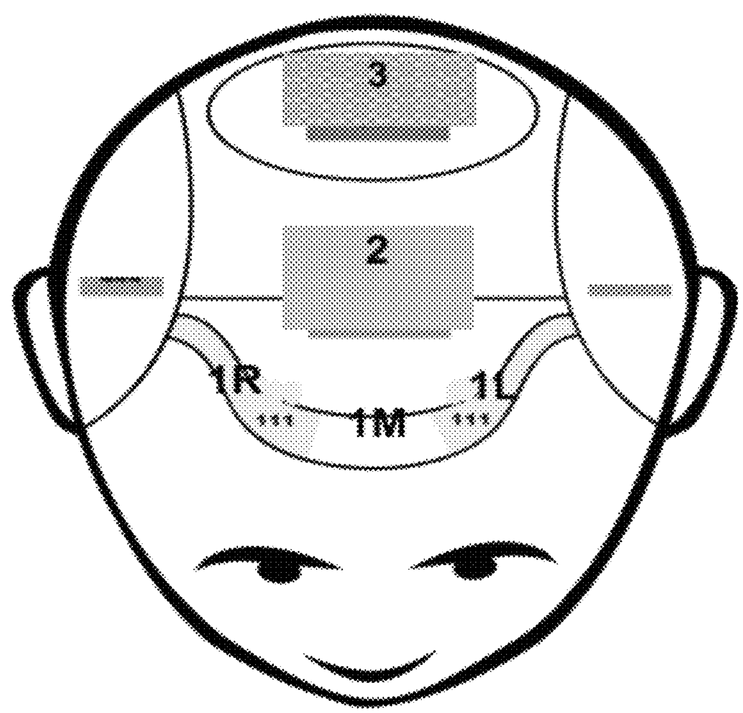
FIG. 4G: A depiction of the hair loss zones referred to in FIGS. 4A-F.

Zone-2 and 4) Zone-3, as shown in FIG. 4G. A 1.1 $cm^2$ area of each zone was shaved followed by a measurement of hair density (hairs per $cm^2$) for each type of hair: thin hair (vellus or miniaturized hair; VH; thickness<40 μm); thick hair (terminal hair; TH; thickness>40 μm) and total hair (VH+TH) with a Phototrichographic system (Folliscope; Hansderma, USA). One ml of a total aqueous extract of *F. benghalensis* (TR1) formulation (10 μg/ml final concentration of TR1 in Williams E basic medium (Williams E basic medium substituted with L-glutamine (2 mmol/L); 1× antibiotic (100 units/ml penicillin, 100 μg/ml streptomycin and 0.25 μg/ml amphotericin) and hydrocortisone (10 ng/ml))+25% glycerol (v/v)) was topically applied about twice-a-day (i.e., 20 μg of total dose per day).

Hair density measurements were taken once every two weeks for each area. Hairs with a diameter less than 40 μm were classified as vellus & miniaturized hairs; hairs with a diameter greater than 40 μm were classified as terminal hairs. Treatment with the TR1-formulation for 6 months resulted in an approximately 146% increase in overall terminal hair density. FIGS. 4A-D depict the density of vellus, miniaturized, terminal and total hairs over the 6 month treatment in zones 1 R and L, 1M, 2 and 3, respectively (zones are depicted in FIG. 4G).

FIG. 4E depicts the density of vellus and miniaturized hair, terminal hair and total hair over 10 months of treatment with the TR1-formulation over a varying dosage as depicted in the horizontal axis.

FIG. 4F shows a visualization of the hair growth in the patient described above. The patient was treated with 20 μg/day TR1 up to month 6, had no treatment from the $6^{th}$ month to the $9^{th}$ month and then was treated with 100 μg/day TR1 from the $9^{th}$ month to the $10^{th}$ month followed by 26 μg/day TR3 from the $10^{th}$ month to the $12^{th}$ month.

Example 5

Topical Application of TR1 Results in New Hairs and Thickened Hairs 2 ml of a 50 μg/ml (100 μg per day) TR1 (total aqueous extract of *F. benghalensis*) formulation was topically applied on a daily basis to the whole balding area of the scalp of a patient for four weeks. Patient presented with male pattern baldness in the crown area (Zone 3-right). Prior to the treatment, a 0.789 $cm^2$ area was shaved to such that the hairs were 0.5 mm in length and phototrichographic measurements of the area were taken including hair density and hair thickness. Hair density and thickness was measured using the Tricoscan® system (phototrichography system from FotoFinder Systems Inc. MA, USA). Following four weeks of treatment, the area was shaved to 0.5 mm again and photographs were taken and each hair follicle unit was manually enumerated at 40× magnification for both new hair and increase in thickness of hair.

Figure 5A:
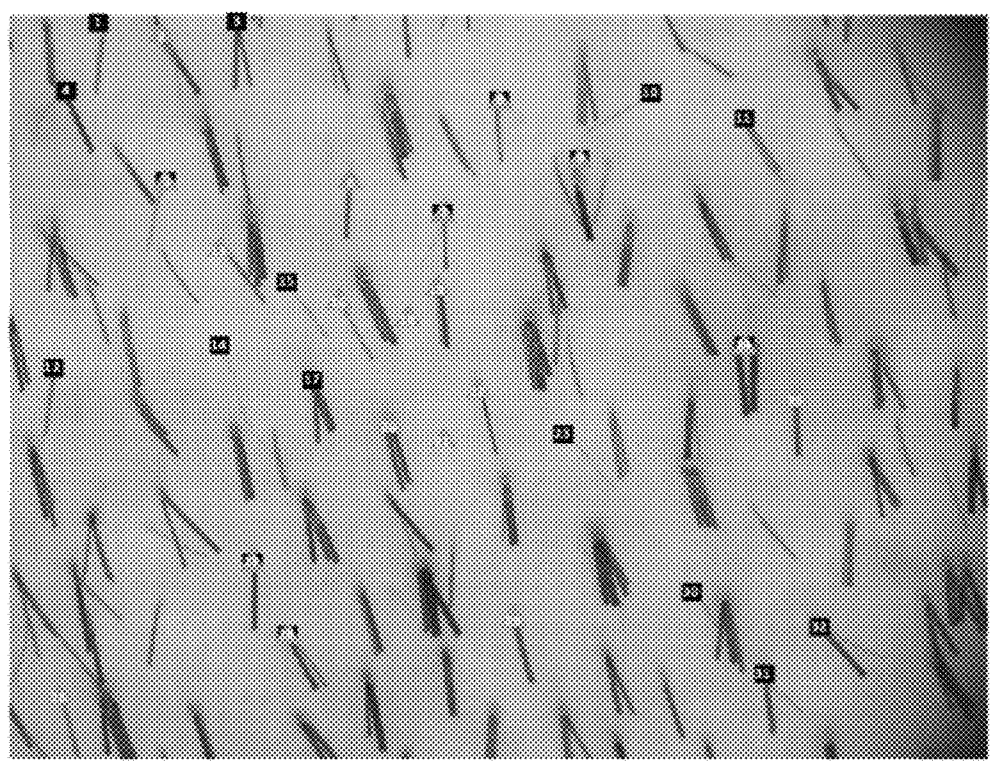
FIG. 5A-5B: A patient (B.D.) treated for one month with a topical formulation containing total aqueous extract of *F. benghalensis* aerial roots (TR1; 100 μg/day) shows growth of new hairs and thickening of pre-existing hairs (5A, before treatment; 5B, after treatment).
Figure 5B:
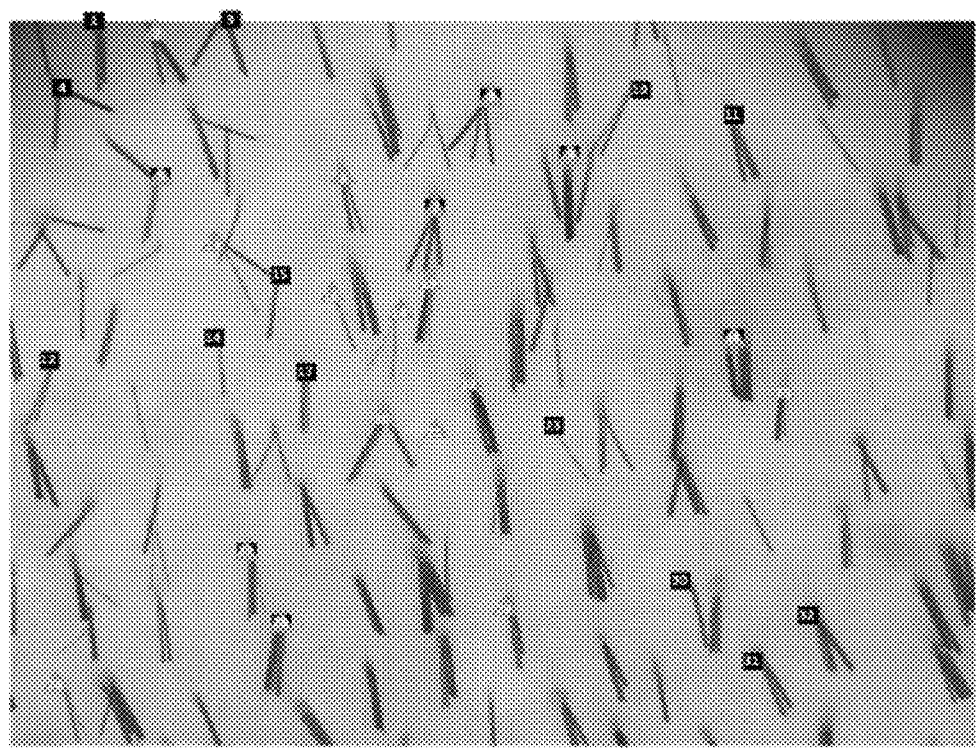

FIG. 5A depicts the treatment zone prior to treatment and FIG. 5B depicts the treatment zone after 4 weeks of treatment. New hairs that appeared after treatment are indicated by numbered triangles and hairs that appeared thickened after treatment are indicated by numbered squares. In all, 9% of the hair follicles in the study area contained hair that was thickened and 10% of the hair follicles in the study area contained new hair. Table 1 contains a detailed analysis of the numbered hair follicles in FIGS. 5A and 5B. Bracketed numbers in the "Increased number" column indicate the number of new hairs at a follicle. Numbers marked with an asterix indicate an entirely new hair (i.e., either a new hair from a new follicle or a new hair from a follicle not previously growing a hair).

TABLE 1

Analysis of the hair follicles in FIGS. 5A and 5B following 4 weeks of treatment with TR1.

| | Changes | | |
|---|---|---|---|
| Hair follicle number | Increased thickness | Increased number | Increased thickness + number |
| 1 | ■ | | |
| 2 | | ▲ (1) | |
| 3 | ■ | | |
| 4 | ■ | | |
| 5 | ■ | ▲ (1) | 1 |
| 6 | | ▲ (1) | |
| 7 | ■ | ▲ (1) | 1 |
| 8 | ■ | ▲ (1) | 1 |
| 9 | ■ | ▲ (1) | 1 |
| 10 | ■ | | |
| 11 | ■ | | |
| 12 | ■ | | |
| 13 | | ▲ (1) | |
| 14 | ■ | | |
| 15 | ■ | | |
| 16 | | ▲ (1) | |
| 17 | ■ | | |
| 18 | | ▲ (2)* | |
| 19 | | ▲ (1) | |
| 20 | | ▲ (1) | |
| 21 | | ▲ (1)* | |
| 22 | | ▲ (2) | |
| 23 | ■ | | |
| 24 | ■ | ▲ (1) | 1 |
| 25 | | ▲ (1) | |
| 26 | | ▲ (1) | |
| 27 | ■ | ▲ (1) | 1 |
| 28 | ■ | ▲ (2) | 1 |
| 29 | | ▲ (1) | |
| 30 | ■ | | |
| 31 | ■ | | |
| 32 | ■ | | |
| Total | 20 | 22 | 7 |
| % Increase | ~9% | ~10% | ~3% |

Example 6

Initial Fractionation of *F. benghalensis* Extract

*F. benghalensis* aerial root tips were oven dried for 2 days at 50° C. until the moisture level was less than 10%. The dried extract was powdered and fractionated by a sequential Soxhlet extraction with five solvents (n-hexane, dichloromethane, ethyl acetate, methanol and water). Approximately 500 ml solvent for each 500 g of dried powder or residue was used. Fractions were extracted for 5 hr and filtered under reduced pressure. Filtrates were dried with nitrogen gas except for the water extract where freeze drying was used.

The fractionation was performed as follows:

(A) An n-hexane extraction was performed on the dried root tips.

(B) The residue from the hexane extract was further extracted with dichloromethane.

(C) The residue from the dichloromethane extraction was further extracted with ethyl acetate.

(D) The residue from the ethyl acetate extraction was further extracted with methanol.

(E) The residue from the methanol extraction was further extracted with water.

Example 7

Analysis of Solvent Fractions

Figure 6:
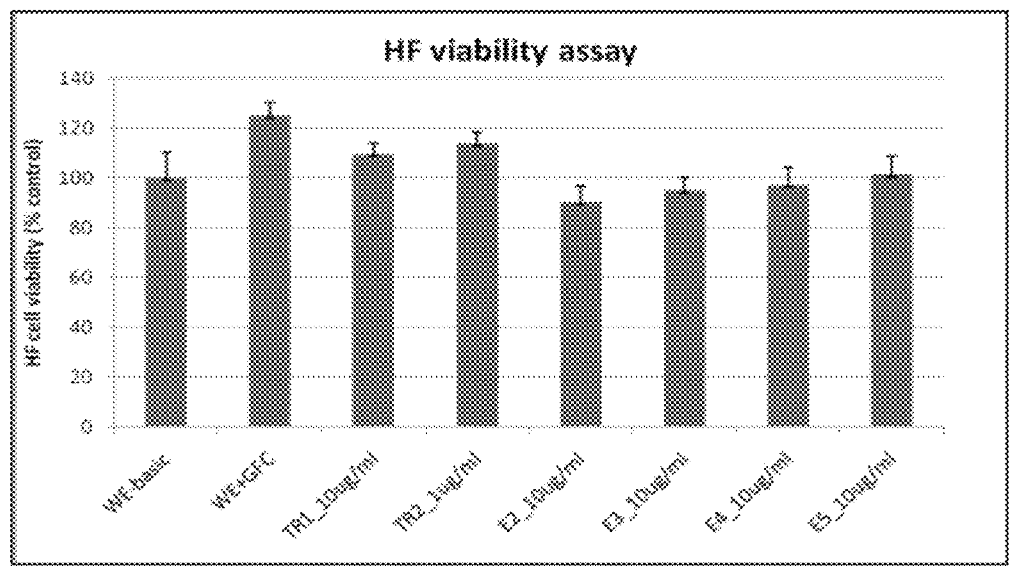
FIG. 6: Hexane extracted fraction E1 of crude extract of *F. benghalensis* (also referred to as TR2) increases hair follicle explant viability at 1 μg/ml.

Each of the five fractions described in Example 6 were tested using a hair follicle explant viability assay (FIG. 6 and Table 2).

Hair follicle explant viability assays were performed as follows: Hair follicles (HF) surgically extracted from volunteers were processed as described before (Example 2). The extracted follicles were plated in 100 μl of appropriate media and incubated for 72 hrs at 37° C. with 5% CO2. To assess hair follicle cell viability after treatment, a MTS (methanethiosulfonate) viability assay was performed: 5 μl MTS reagents (Promega, Wis.) were added per 100 μl HF containing media. Hair follicles were incubated further for 2 hrs at the end of which OD at 490 nm was measured spectrophotometrically Results shown are the Mean±SEM from eight independent experiments performed on hair follicles from eight different patients. In each experiment, at least 4-6 hair follicles were used per treatment per patient. Hence each experimental point represents the Mean±SEM of 8 independent experiments performed on hair follicles from 8 different patient samples. The different treatments are labeled as follows:

TR1 (CE Crude Extract), Total aqueous extract of *F. benghalensis*

TR2 (E1), n-Hexane extracted fraction

E2, Dichloromethane (DCM) extracted fraction

E3, Ethyl acetate (EtOAc) extracted fraction

E4, Methanol (MeOH) extracted fraction

E5, Water extracted fraction

WE-basic refers to Williams-E basic medium (Sigma-Aldrich, Canada), WE+GFC refers to nine growth factors each at 20 ng/ml and hypoxanthine at 2 μM final concentration.

Treatment with TR2 (hexane extracted fraction-E1) resulted in an approximately 14% increase in hair follicle viability at 1 μg/ml compared to the untreated control. The total aqueous extract of *F. benghalensis* (TR1), demonstrated an approximately 10% increase in HF viability at 10 μg/ml (compared to 1 μg/ml for TR2).

TABLE 2

Hair follicle viability assay for solvent fractions TR1, TR2 (E1) and E2-5

| Treatment | Overall viability (% control) Mean | SEM |
|---|---|---|
| WE-basic | 100 | 10.33909 |
| WE + GFC | 125.0721 | 5.162223 |
| TR1_10 μg/ml | 109.5897 | 4.179249 |
| TR2_1 μg/ml | 113.776 | 4.505491 |
| E2_10 μg/ml | 90.21753 | 6.321347 |
| E3_10 μg/ml | 95.0384 | 5.156974 |
| E4_10 μg/ml | 97.25792 | 7.175035 |
| E5_10 μg/ml | 101.3029 | 7.33428 |

Figure 7:
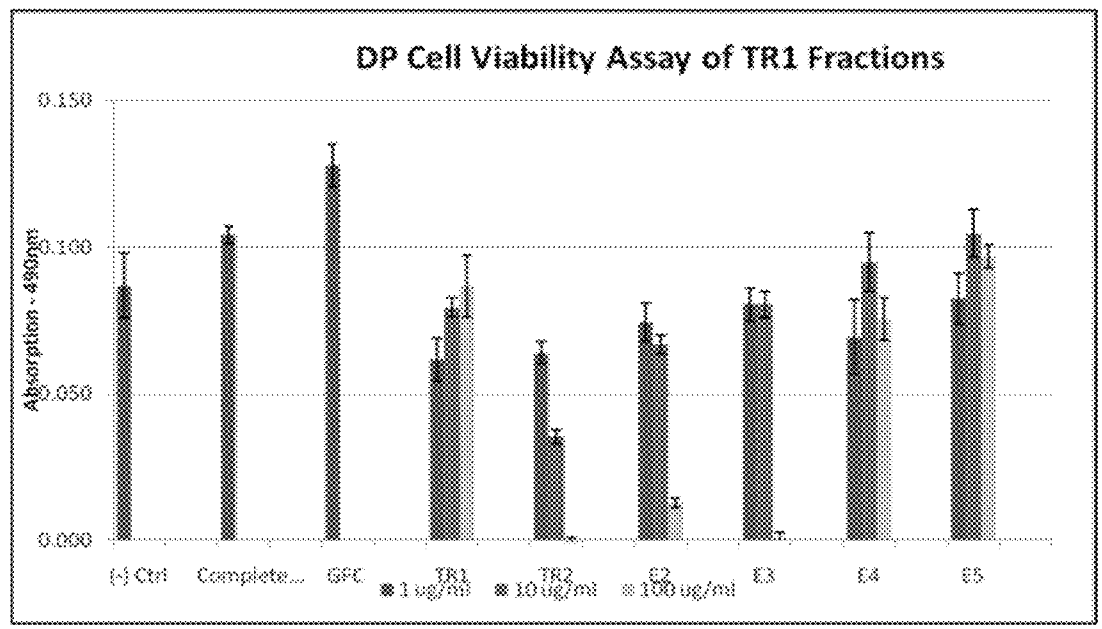
FIG. 7: Water extracted fraction E5 of crude extract of *F. benghalensis* increases dermal papilla (DP) cell viability.

Dermal papillae (DP) cell viability assays were performed as described above in Example 3 (FIG. 7). Each experimental point represents the Mean±SEM of eight replicates from pooled cells of eight patients. "Ctl" refers to basic medium; "complete medium" is optimum cell culture medium for human DP cells; "GFC" is basic medium plus nine growth factors at 20 ng/ml, and hypoxanthine at 2 μM final concentration. TR1 and TR2, E2, E3, E4, E5 are labeled as in FIG. 6. Fractions E4 (methanol extracted) and E5 (water extracted) showed 9% and 20% increase in DPC viability, respectively, at 10 μg/ml compared to basic medium. Furthermore, E5 appears to be as potent as the complete medium in promoting DP cell viability. Therefore, E5 may contain compounds that are highly efficacious in promoting DP cell viability and/or proliferation and which may have commercial applications.

Figure 8:
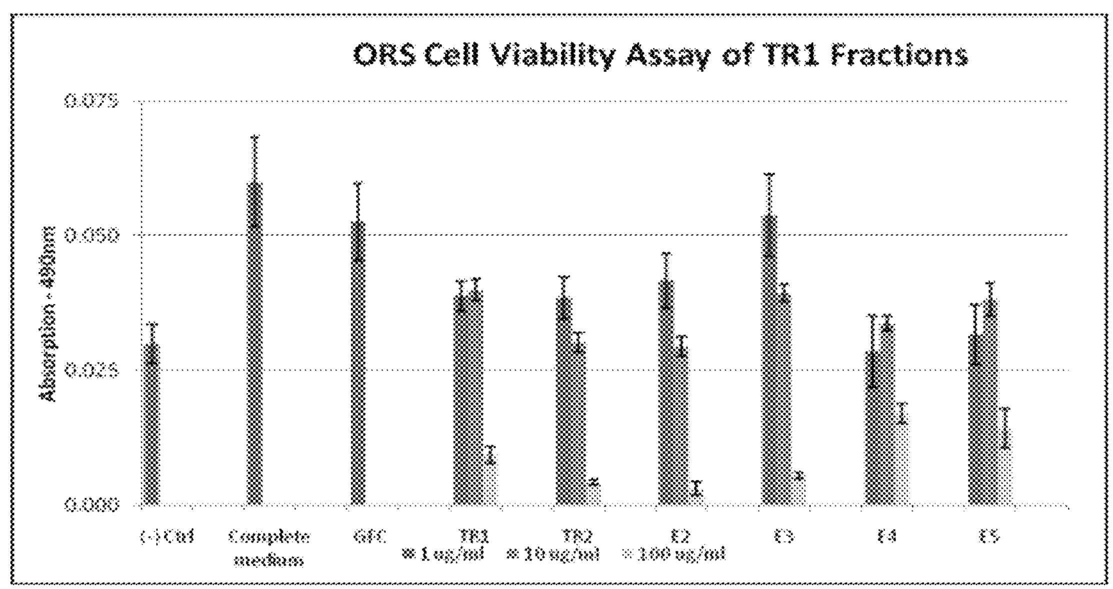
FIG. 8: Ethyl acetate extracted fraction E3 of crude extract of *F. benghalensis* increases outer root sheath (ORS) cell viability.

Outer root sheath (ORS) cell viability assays were performed as follows (FIG. 8): Outer root sheath (ORS) cells were isolated from hair follicles. The cells were plated and treated with the total aqueous extract (TR1) for different durations by incubating at 37 with 5% $CO_2$. To assess cell viability after treatment, the MTS viability assay was performed as described in Example 3. Each experimental point represents the Mean±SEM of eight replicates from pooled cells of ten patients. "Ctl" refers to basic medium; "complete medium" is optimum cell culture medium for human ORS cells; "GFC" is basic medium plus nine growth factors at 20 ng/ml, and hypoxanthine at 2 μM final concentration. TR1 and TR2, E2, E3, E4, E5 are labeled as in FIG. 6. The E3 fraction (ethyl acetate) showed the best positive results with approximately 80% increase in viability at 1 μg/ml, compared to the untreated controls.

A sub-population of the outer root sheath cells includes epidermal stem cells (eSc), which reside in the epidermal bulge of the hair follicle. Without being bound by theory, because outer root sheath cell viability is increased by the ethyl acetate fraction (E3), it is predicted that E3 also increases the viability of epidermal stem cells, optionally by increasing eSC proliferation.

Example 8

Characterization of the Hexane Extracted Fraction E1 (TR2)

Activity of TR1 and TR2

The ability of the hexane extracted E1 fraction (TR2) compared to the total aqueous extract TR1 to promote hair follicle explant viability over different concentrations is shown in Table 3, below. Data is compared to a no-treatment control (WE-Basic medium).

Figure 9:
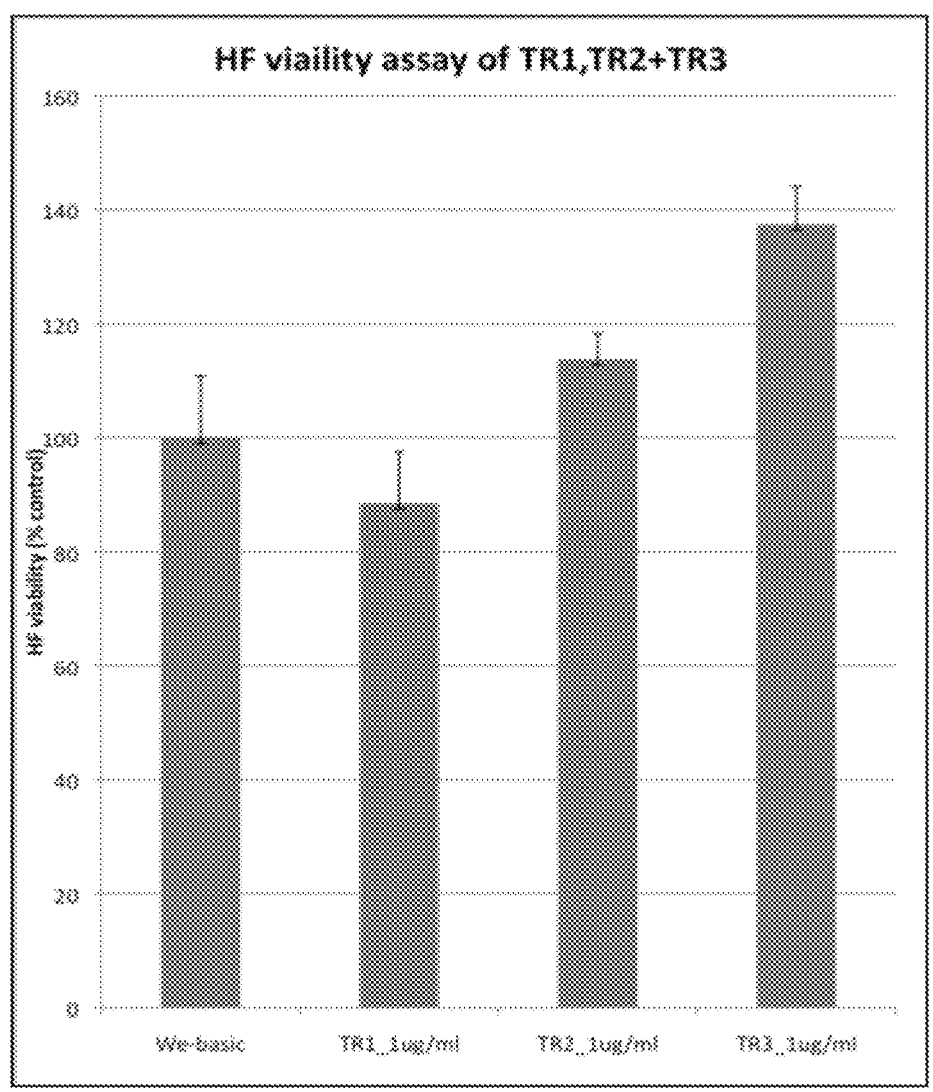
FIG. 9: Hair follicle explant viability assay of the total aqueous extract of *F. benghalensis* (TR1), the hexane extracted fraction E1 (TR2) and TR3 at 1 μg/ml.

FIG. 9 depicts a hair follicle explant viability assay for TR1, TR2 and TR3 at 1 μg/ml. TR3 is described below in Example 11. At 1 μg/ml TR3 promotes greater hair follicle viability than TR2, and TR2 promotes greater hair follicle viability than TR1. Each data point represents Mean±SEM for 4-6 replicates from 3-8 donors.

TABLE 3

Hair follicle viability assay for TR1,* TR2 and TR3.

| Treatment | *Mean ± SEM of HF viability (% control) | | |
|---|---|---|---|
| Concentration | 1 μg/ml | 10 μg/ml | 100 μg/ml |
| TR1 | 88.5 ± 9.03 | 109.6 ± 4.2 | 69.7 ± 16.1 |
| TR2 | 113.8 ± 4.5 | 95.9 ± 4.03 | 95.5 ± 8.4 |
| TR3 | 137.3 ± 6.7 | 103.4 ± 4.6 | 83.7 ± 9.9 |

*Represents Mean ± Standard deviation of Mean (SEM) for 4-6 replicates derived from HF viability/growth assays of 3-8 donors.

Topical Application of TR2 Increases Hair Density

A 2.2 $cm^2$ area of zone 2M (zone 2—middle) of a patient's (M.A.F.) scalp was shaved followed by a measurement of hair density over a 0.789 $cm^2$ area (hairs per $cm^2$) for each type of hair: thin hair (vellus/miniaturized hair; VH); thick hair (terminal hair; TH) and total hair (VH+TH) with the Tricoscan system (FotoFinder, USA). Hairs with a diameter of less than 40 μm were characterized as vellus and miniaturized hair.

Figure 10:
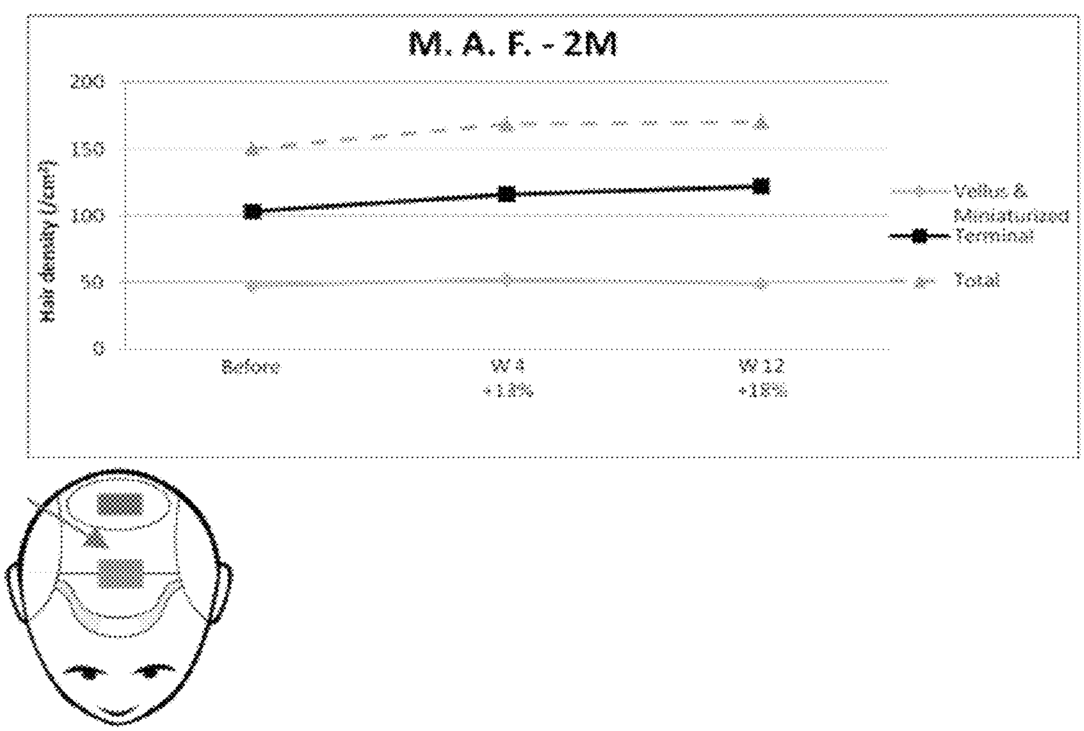
FIG. 10: A patient (M.A.F.) treated for one month with a topical formulation containing hexane extracted fraction E1 of crude extract of *F. benghalensis* (TR2; 20 μg/day) shows an increase in terminal hair density and vellus and miniaturized hair density.

Hairs with a diameter greater than 40 μm were characterized as terminal hairs. One ml of TR2 formulation (10 μg/ml TR2 in Williams E+25% glycerol) was topically applied about twice-a-day (total dose, 20 μg/day). Hair density measurements were taken after 12 weeks of treatment. As shown in FIG. 10, treatment with the TR2-formulation for 12 weeks resulted in an approximately 18% increase in overall terminal hair density.

Topical Application of TR2 Results in New Hairs and Thickened Hairs

Figure 11A:
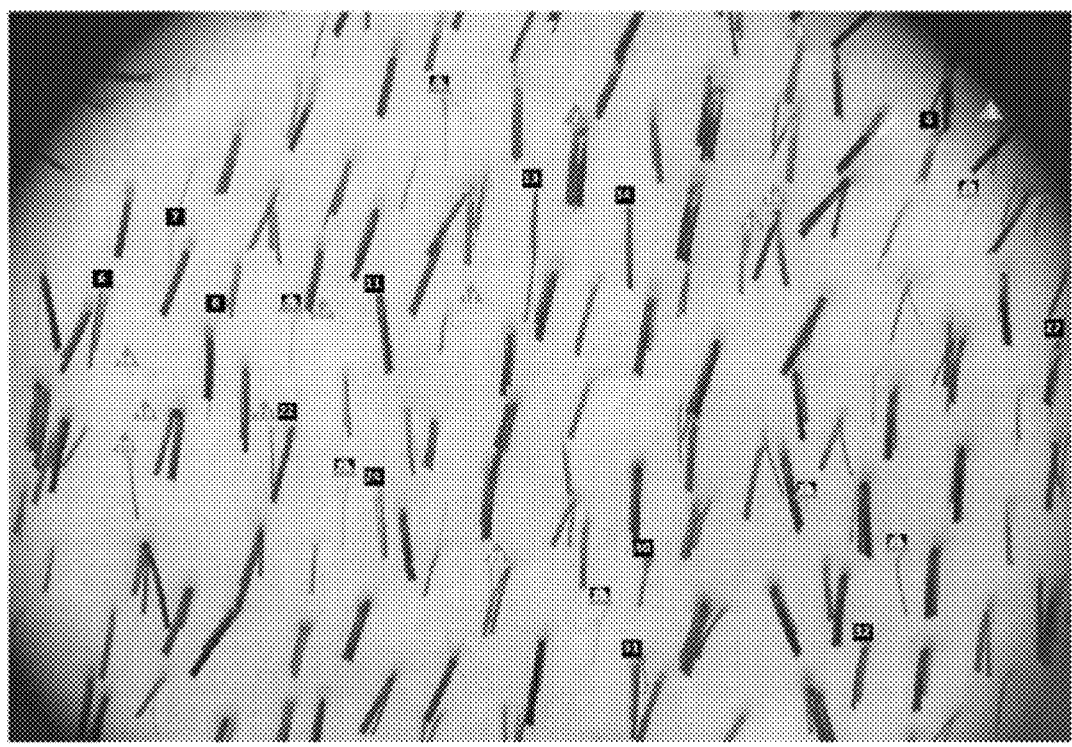
FIG. 11A-B: A patient (M.A.F.) treated for one month with a topical formulation containing hexane extracted fraction E1 of crude extract of *F. benghalensis* (TR2; 20 μg/day), shows growth of new hairs and thickening of pre-existing hairs (11A, before treatment; 11B, after treatment).
Figure 11B:
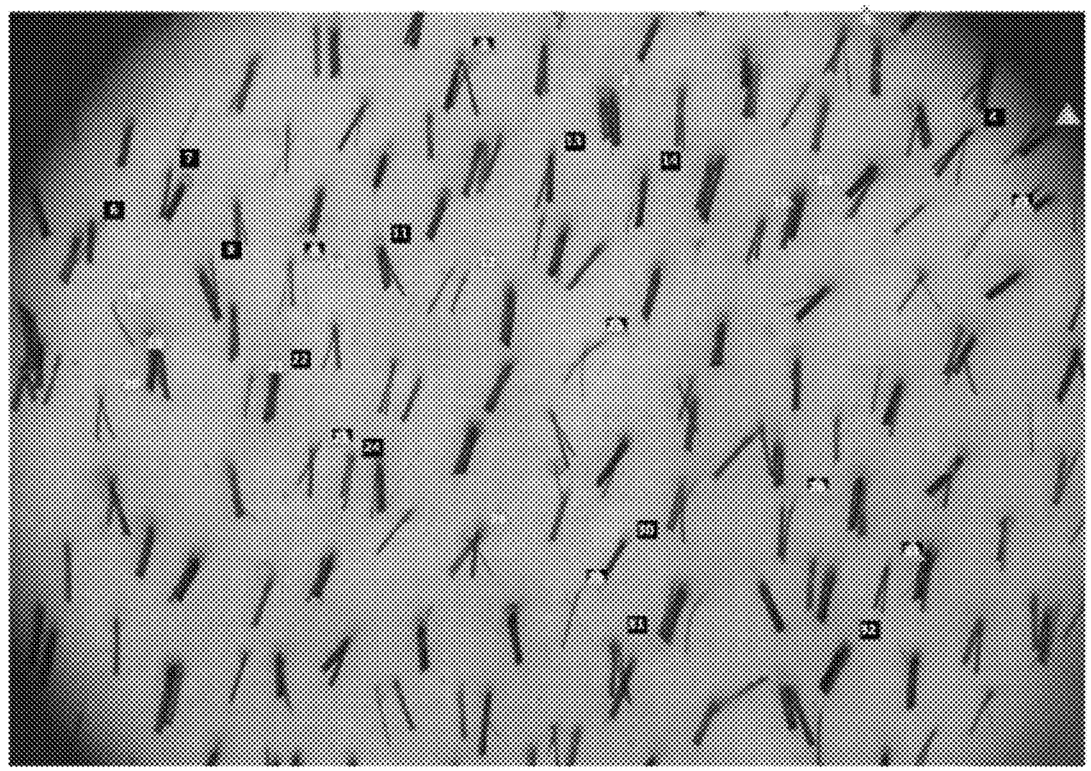

Two ml of a 10 μg/ml TR2 formulation was topically applied on a daily basis to all bald zones of the scalp of patient M.A.F. for four weeks. Prior to the treatment, the area was shaved to such that the hairs were 0.5 mm in length and photographs of the area where taken. Hair density and hair thickness was measured using the Tricoscan system. Following four weeks of treatment, the area was shaved to 0.5 mm again and phototrichography was performed and hair density measured. Also, new hair and thickening of hair were manually enumerated. FIG. 11A depicts the treatment zone prior to treatment and FIG. 11B depicts the treatment after 4 weeks of treatment. New hairs that appeared after treatment are indicated by numbered triangles and hairs that appeared thickened after treatment are indicated by numbered squares. In all, 9% of the hair follicles in the study area contained hair that was thickened and 10% of the hair follicles in the study area contained new hair. Table 4 contains a detailed analysis of the numbered hair follicles in FIGS. 11A and 11B. Bracketed numbers in the "Increased number" column indicate the number of new hairs at a follicle. Numbers marked with an asterix indicate an entirely new hair (i.e., either a new hair from a new follicle or a new hair from a follicle not previously growing a hair).

TABLE 4

Analysis of the hair follicles in FIGS. 11A and 11B following 4 weeks of treatment with TR2.

| Hair | Changes | | Increased thickness |
|---|---|---|---|
| follicle number | Increased thickness | Increased number | and number |
| 1 | ■ | ▲ (3) | 1 |
| 2 | | ▲ (1) | |
| 3 | | ▲ (1) | |
| 4 | ■ | | |
| 5 | | ▲ (2) | |
| 6 | ■ | | |
| 7 | ■ | | |
| 8 | ■ | | |
| 9 | ■ | ▲ (1) | 1 |
| 10 | | ▲ (1)* | |
| 11 | ■ | | |
| 12 | | ▲ (1) | |
| 13 | ■ | | |
| 14 | ■ | | |
| 15 | | ▲ (1) | |
| 16 | | ▲ (1) | |
| 17 | ■ | ▲ (1) | 1 |
| 18 | | ▲ (1) | |
| 19 | | ▲ (1)* | |
| 20 | | ▲ (1) | |
| 21 | | ▲ (1) | |
| 22 | ■ | | |
| 23 | ■ | ▲ (1) | 1 |
| 24 | ■ | | |
| 25 | | ▲ (1)* | |
| 26 | ■ | ▲ (1) | 1 |
| 27 | ■ | | |
| 28 | | ▲ (1) | |
| 29 | ■ | ▲ (1) | 1 |
| 30 | ■ | | |
| 31 | ■ | | |
| 32 | ■ | ▲ (1) | 1 |
| 33 | ■ | | |
| Total | 20 | 23 | 7 |
| % Increase | ~9% | ~10% | ~5% |

Example 9

Small-Scale Sub-Fractionation of the Hexane Extracted Fraction Using HPLC

The hexane extracted fraction E1 of the crude extract (TR2) was further fractionated into 30 sub-fractions (e1 to e30) using high performance liquid chromatography (HPLC).

Figure 12:
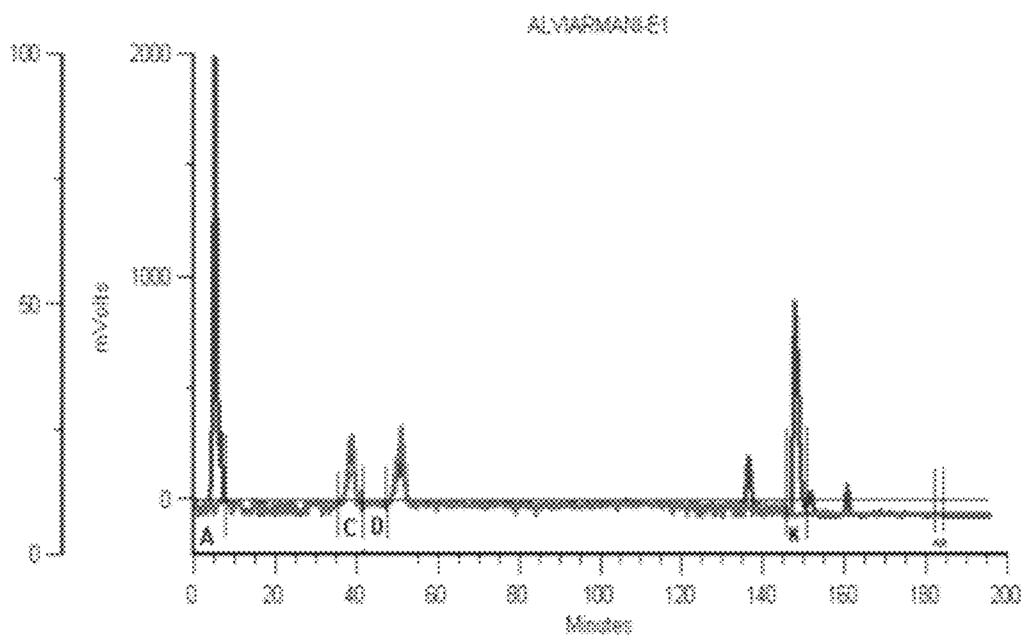
FIG. 12: HPLC/UV chromatogram depicting sub-fractionation of n-hexane extracted fraction E1 (TR2).

The n-hexane fraction E1 (TR2; 408 mg) was dissolved in DMSO/methanol and insoluble material was removed by centrifugation. The supernatant was injected onto a Gilson HPLC system and separated by reverse-phase preparative HPLC [Waters Xterra PrepMS, C18 Column 10 μm, 19×300 mm, gradient elution: solvent A (0.1% HCOOH in H2O): B (0.1% HCOOH in ACN) 80:15→30:70 over 140 min, flow rate 18 mL/min, 30:70→0:100 over 40 min, flow rate 18 mL/min]. The corresponding HPLC/UV chromatogram is shown in FIG. 12.

Figure 13:
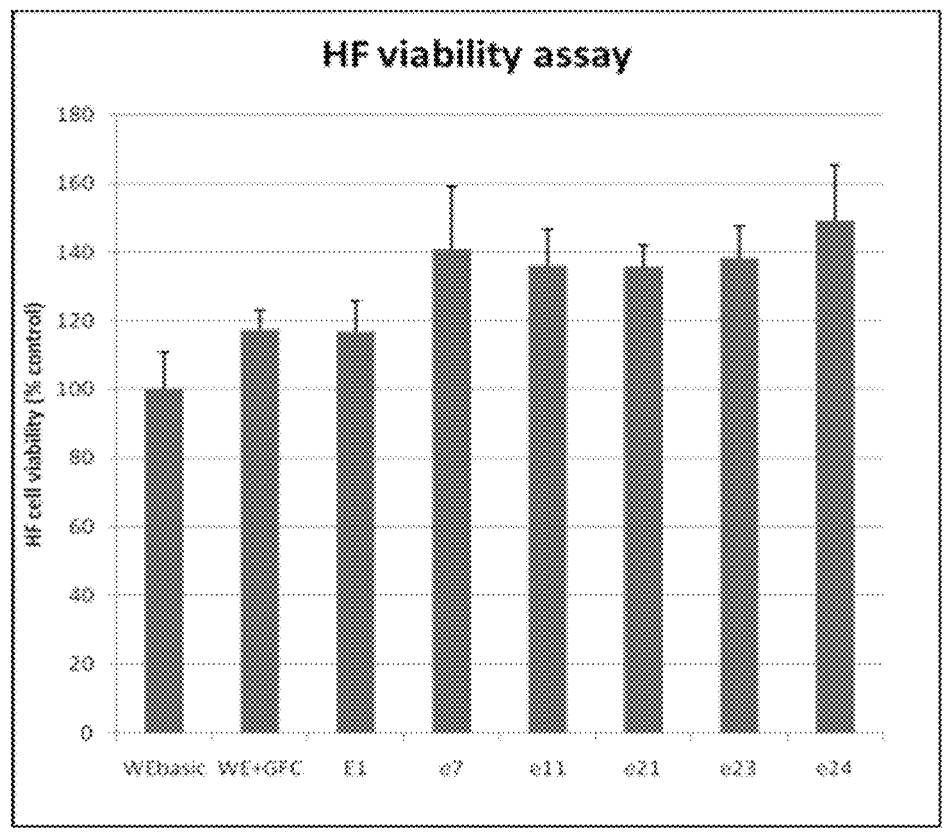
FIG. 13: Sub-fractions e7, e11, e21, e23 and e24 have higher hair follicle viability promoting activity compared to the hexane extracted parent fraction, E1 (TR2).

Thirty fractions (e1 to e30) were collected, dried and tested with hair follicle explant viability assays as described above in Example 7. Results are shown in FIG. 13 and Table 5. Each data point represents the mean±SEM of 4 experiments from 4 different patients. E1 (TR2) is the E1 fraction of TR1 (1 μg/ml) and e1 to e30 are the sub-fractions of E1 (1 μg/ml). WEbasic is William's E basic medium and WE+GFC is WEbasic supplemented with nine growth factors (each at 20 ng/ml) and hypoxanthine (2 μM).

Sub-fractions e7 (HPLC retention time 183.6-184.1 min), e11 (HPLC retention time 146.6-150 min), e21 (HPLC retention time 0.6-8.1 min), e23 (HPLC retention time 37.1-40.1 min) and e24 (HPLC retention time 40.1-48.6 min) all showed higher HF viability promoting activity compared to the parent fraction, E1. Sub-fraction e7 showed a 41% increase in activity compared to the control, sub-fractions ell and e21 showed a 36% increase, fraction e23 showed a 38% increase and fraction e24 showed a 49% increase.

TABLE 5

Hair follicle viability assay for sub-fractions e1-e30.

| | Mean | SEM |
|---|---|---|
| WEbasic | 100 | 10.87846 |
| WE + GFC | 117.4787 | 5.497826 |
| E1 (TR2) | 116.8535 | 8.899688 |
| e1 | 122.0187 | 9.297722 |
| e2 | 114.2366 | 13.68656 |

TABLE 5-continued

Hair follicle viability assay for sub-fractions e1-e30.

| | Mean | SEM |
|---|---|---|
| e3 | 105.6424 | 10.5447 |
| e4 | 100.5444 | 5.60976 |
| e5 | 113.6869 | 9.208996 |
| e6 | 108.5335 | 25.84826 |
| e7 | 140.8913 | 18.16538 |
| e8 | 111.9571 | 14.37061 |
| e9 | 90.59237 | 9.773622 |
| e10 | 100.4393 | 18.47976 |
| e11 | 135.9675 | 10.69667 |
| e12 | 92.04656 | 10.89928 |
| e13 | 111.4193 | 10.056 |
| e14 | 114.1666 | 4.548484 |
| e15 | 113.1492 | 5.870526 |
| e16 | 121.7312 | 14.16937 |
| e17 | 99.05599 | 9.613711 |
| e18 | 119.8706 | 6.869545 |
| e19 | 119.4158 | 15.89165 |
| e20 | 116.773 | 10.31464 |
| e21 | 135.6538 | 6.220953 |
| e22 | 124.459 | 12.83294 |
| e23 | 138.1927 | 9.489146 |
| e24 | 149.1294 | 16.21481 |
| e25 | 110.2886 | 11.21971 |
| e26 | 115.0458 | 8.111034 |
| e27 | 116.0353 | 8.023802 |
| e28 | 126.587 | 6.219617 |
| e29 | 106.268 | 8.50038 |
| e30 | 113.8059 | 8.50038 |

Further chemical characterization of the sub-fractions was performed by isolating five of the active sub-fractions with analytical LC (liquid chromatography) followed by analysis with HR-ESI-MS (High Resolution Mass Spectroscopy; Burker microQTOF) followed by $^{1}$H-NMR analysis.

1. Sub-Fraction e7/187AA (Sub-Fraction of TR2)

A yield of 0.2 mg of sub-fraction e7 was recovered by preparative HPLC. Sub-fraction e7 contains a mixture of very non-polar compounds including cerebrosides and other compounds.

2. Sub-Fraction e11/187K (Sub-Fraction of TR2)

A yield of 23.3 mg of sub-fraction e11 was recovered by preparative HPLC. Sub-fraction e11 contains a mixture of non-polar compounds. Although the LC profile suggested a single peak, $^{1}$H-NMR revealed a mixture of several compounds including saturated and unsaturated fatty acids, terpenes and other compounds.

The e11/187K fraction was further HPLC fractionated by reverse-phase HPLC [Phenominex, Luna, Phenyl-hexyl column 5 μm, 21.2×150 mm gradient elution: solvent A (0.1% Formic acid in water): B (0.1% Formic acid in ACN) 60:40→40:60 over 30 min, flow rate 18 ml/min, 40:60→0:100 over 60 min, flow rate 18 ml/min]. Out of the seventeen sub sub-fractions, the fraction with the highest activity as assessed using hair follicle explant assays was further subjected to $^{1}$H NMR and HR-ESI-MS analysis which confirmed the presence of saturated dicarboxylic acid, with azelaic acid as the major compound. Subsequent analysis with 2D NMR procedures: COSY, HSQC and HMBC confirmed the structure of azelaic acid.

3. Sub-Fraction e21 (Sub-Fraction of TR2)

A yield of 4.1 mg of sub-fraction e21 was recovered by preparative HPLC. Sub-fraction e21 contains a mixture of polar disaccharides.

4. Sub-Fraction e23 (Sub-Fraction of TR2)

A yield of 9.5 mg of sub-fraction e23 was recovered by preparative HPLC. Analysis with LC revealed a single component accounting for 95% of the mass and further analysis with 1- and 2-D NMR revealed the compound to be psoralen. Analysis with 2D NMR procedures: COSY, HSQC and HMBC confirmed the structure of psoralen.

5. Sub-Fraction e24 (Sub-Fraction of TR2)

A yield of 2 mg of sub-fraction e24 was recovered by preparative HPLC. Sub-fraction e24 contains a mixture of coumarins (analogues of psoralen) and other compounds.

Example 10

Large-Scale Sub-Fractionation of the Hexane Extracted Fraction through Solvent Partition and Open Column Vacuum-Assisted Liquid Chromatography In a parallel analysis, 16.2 g of E1 extract was suspended in methanol-water (2:1, 0.3 L) and then partitioned with chloroform to give a chloroform soluble fraction (15.2 g, 206A) and an aqueous soluble fraction. The aqueous soluble fraction was evaporated to dryness and partitioned with butanol-water (1:1, 0.2 L) to give a butanol soluble fraction (0.4 g, 206B) and an aqueous fraction (0.6 g, 206C). A portion of chloroform soluble fraction (15.1 g) was chromatographed on a Silica gel (Merck 9385, 800 g, 10×24 cm) vacuum-assisted liquid chromatography (VLC) column and initially eluted with n-hexane (100% hexane, 207A, 2 L), n-hexane-chloroform (80:20, 207B to 0:100, 207P each 1 L), chloroform-methanol (100:0, 207P to 50:50, 207AD each 1 L) and finally methanol (100%, 1 L) to give 31 fractions. The 31 sub-fractions were obtained and were labeled 207A to 207AE.

Figure 14:
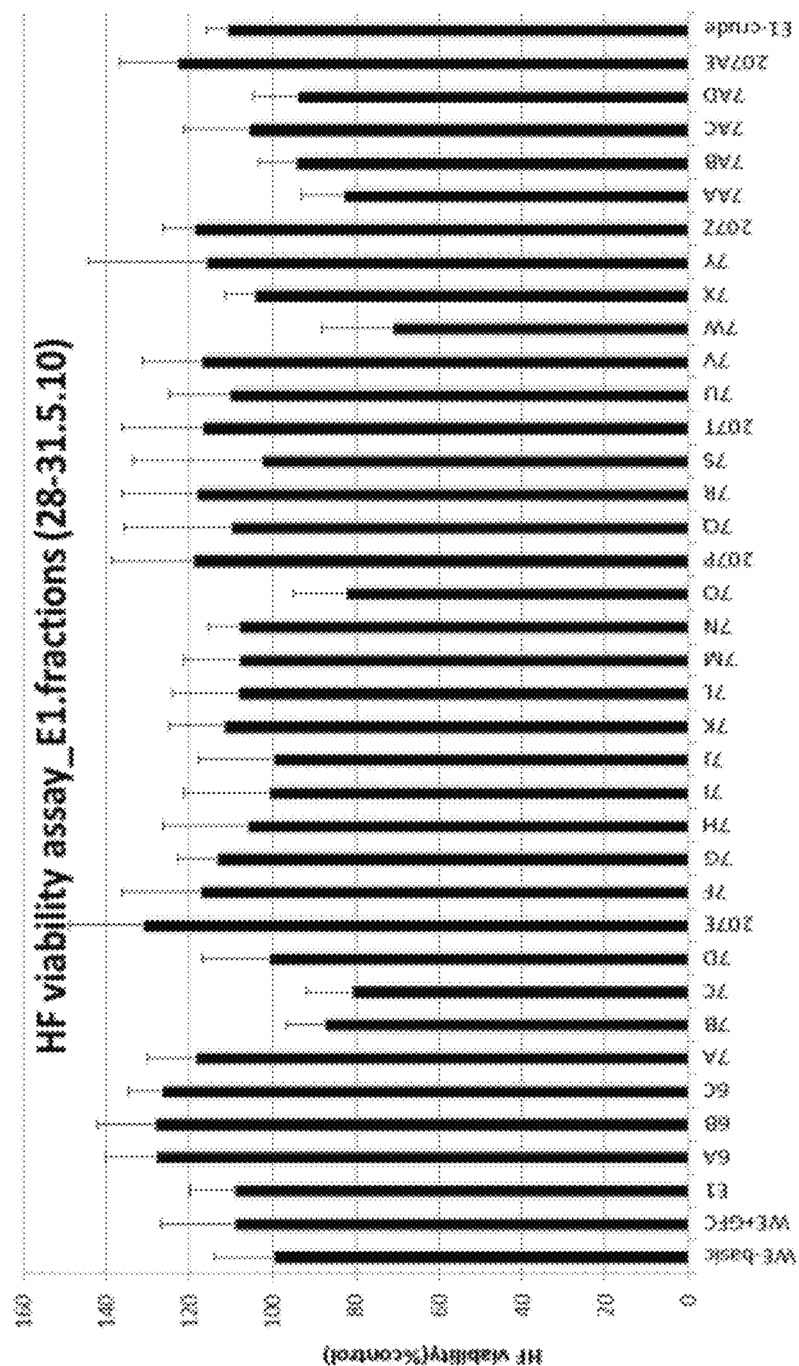
FIG. 14: Hair follicle viability assay for large scale E1(TR2) fractions. E1 (TR2) was sequentially partitioned and the resulting chloroform fraction was further separated into sub-fractions by vacuum-assisted liquid chromatography. WE-basic refers to Williams-E basic medium, WE+GFC refers to nine growth factors each at 20ng/ml and hypoxanthine at 2 μM final concentration. All fractions are at 1 μg/ml concentration. Each point represents the mean +/−SEM of 3-5 hair follicles from 3 different patients.
Figure 15:
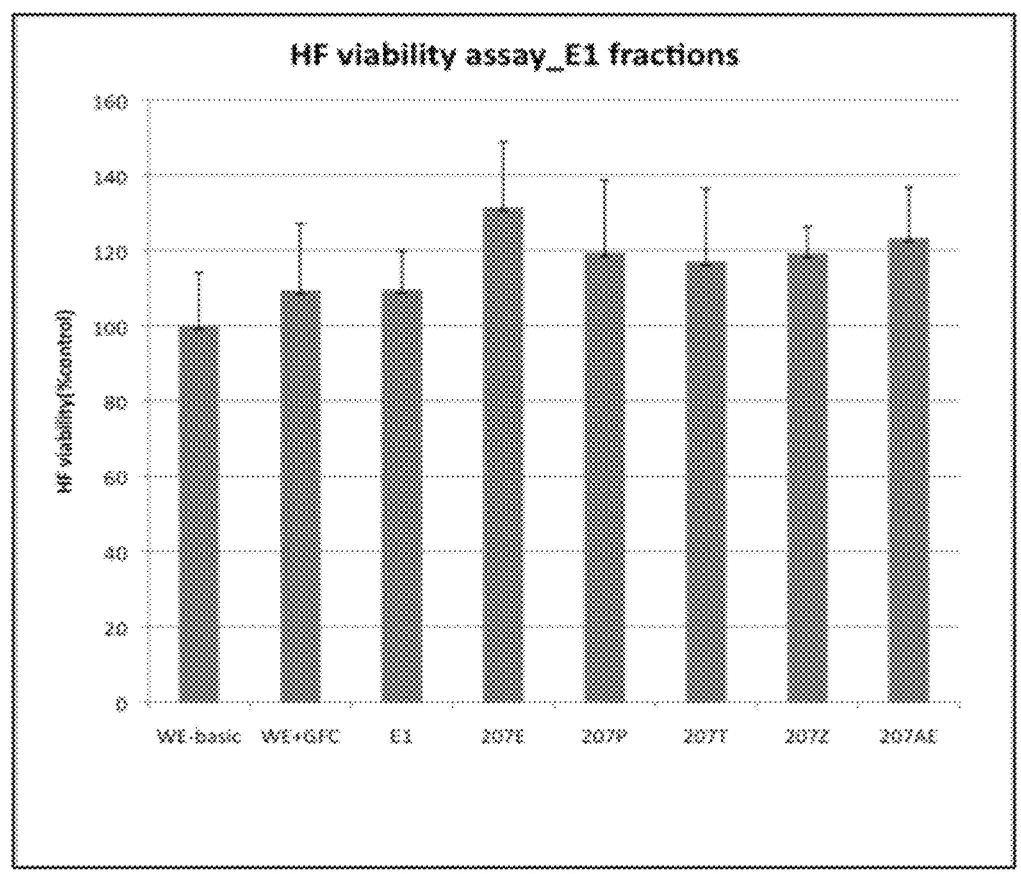
FIG. 15: Hair follicle explant viability assay on 5 sub-fractions of hexane extracted fraction E1 (TR2).

Each of the 31 sub-fractions were individually investigated for promotion of hair follicle viability using the hair follicle explant viability assay system described above in Example 7 and the results are shown in FIG. 14. As also detailed in FIG. 15, treatment of hair follicle explants with 1 μg/ml of each of sub-fractions 207E, 207P, 207T, 207Z and 207AE increased the viability of the hair follicle explants compared to the control. Each point represents the Mean±SEM of 3-5 hair follicles from 3 different patients. E1 is the E1 fraction of TR1 (1 μg/ml). WEbasic is William's E basic medium and WE+GFC is WEbasic supplemented with nine growth factors (each at 20 ng/ml) and hypoxanthine (2 μM).

Figure 16:
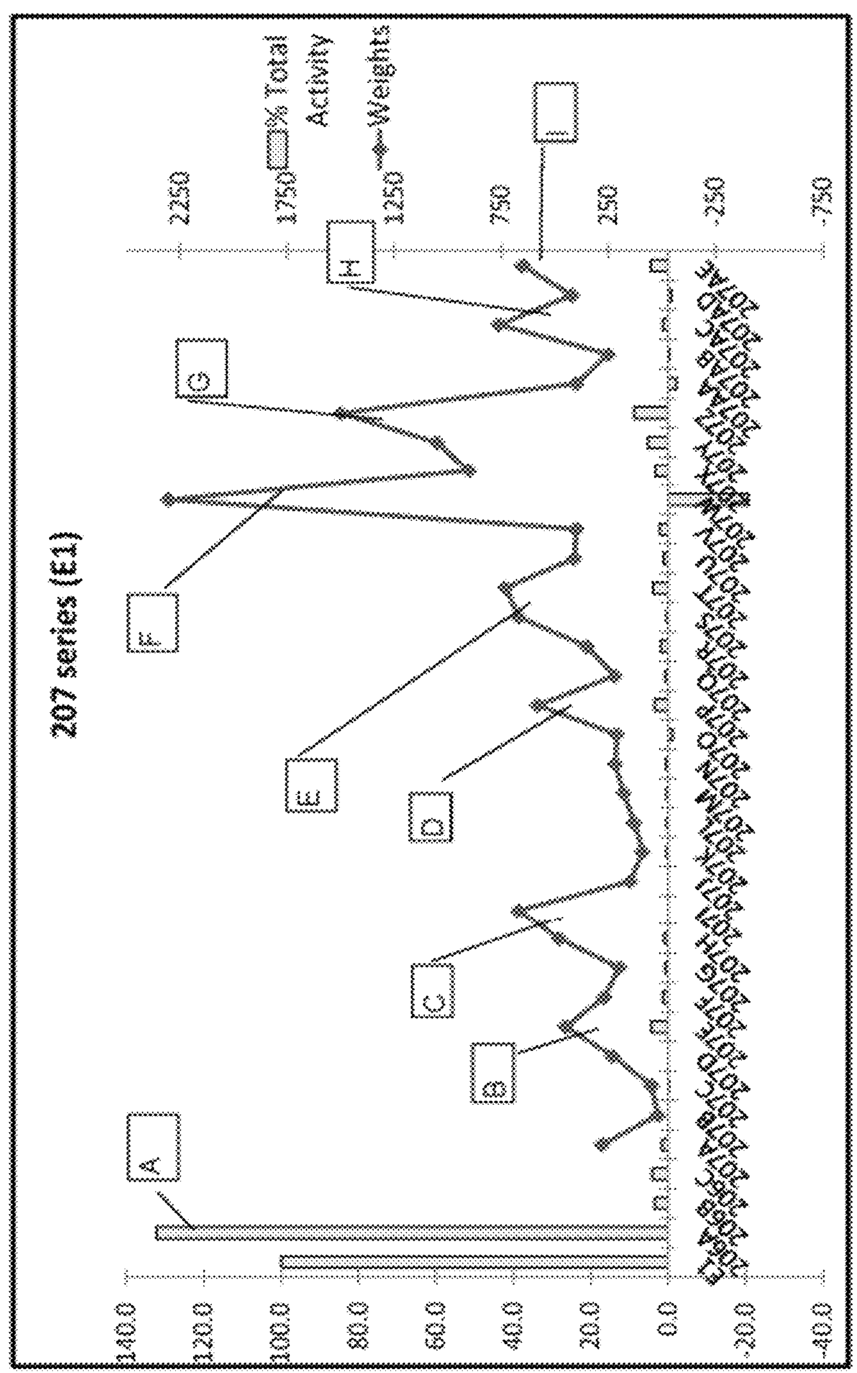
FIG. 16: Hair follicle viability assay for large scale E1 (TR2) fractions, normalized with respect to the relative weight of the fractions. Letters indicate components and descriptors of the various fractions: A: solvent front, polar actives; B: saturated ester waxes; C: unknown, inactive; D: 5-methomsoralens, lupeol, cvcloartenol, α-amyrin; E: stipmasterol and β-sitosterol; F: unsaturated fatty acids (e.q. linoleic acid), negative activity; G: palmitic acid, betulonic acid, betulinic acid; H: unknown, inactive; I:cerebrosides and 13-hyoxy-9,11-octadecadienoic acid.

The data was also normalised with respect to fraction weights such that the activity of each fraction could be represented proportional to its contribution to the activity of the whole extract. The normalised data is shown in FIG. 16.

Table 6 depicts the solvent system used for the elution of each sub-fraction 207E, 207P, 207T, 207Z and 207AE, the total yield, the activity per mg of each sub-fraction 207E, 207P, 207T, 207Z and 207AE and the total activity of each sub-fraction (weight of fraction times activity per milligram).

Activity is defined as the % increase in hair follicle viability compared to the control treatment (WE-basic). Calculations are performed as follows: For example, for E1: E1 increases HF viability by 10%. 10/100×16120 mg (weight of E1)=1612 total activity.

TABLE 6

Elution details and activity of sub-fractions 207E, 207P, 207T, 207Z and 207AE.

| Fraction | Mobile phase (solvent gradient) | Yield (mg) | Total Activity | Activity/ mg | Total Activity (% E1) |
|---|---|---|---|---|---|
| E1/TR2 | | 16120 | 1612 | 0.1 | 100 |
| 207E | Hexane:Chloroform (70:30) | 450 | 139.5 | 0.31 | 310 |
| 207P | Chloroform (100%) | 580 | 110.2 | 0.19 | 190 |
| 207T | Chloroform:Methanol (98:2) | 730 | 124.1 | 0.17 | 170 |
| 207Z | Chloroform:Methanol (97:3) | 1500 | 285 | 0.19 | 310 |
| 207AE | Methanol (100%) | 650 | 143 | 0.22 | 220 |

Analysis of Active Fractions from the Fractionation of Crude E1 Extract (207 Series)

The active fractions from the large scale fractionation of E1 were analysed by analytical LC (Agilent 1100), 1H NMR (Bruker 500 MHz) and HR-ESI-MS (Bruker microQTOF). The results are summarised in Table 7. Mixtures containing psoralens, saturated and unsaturated fatty acids, stigmasterol and β-sitosterol, betulinic, betulin, betulonic acids, cerebrosides and other compounds were identified using these techniques.

TABLE 7

Results for active fractions from 207 series.

| Sample ID | Mobile phase (Solvent gradient) | Fraction mass (mg) | HR-ESI-MS | Comment |
|---|---|---|---|---|
| AAGE1-Mp288-206A Parent of 207 Solvent Partition Chloroform fraction | | 15200 | | Chloroform enriched fraction after solvent partition and were subjected to Vacuum Liquid Chromatography (VLC) silica gel column to give 31 fractions ( Mixture. |
| AAGE1-Mp288-206B Solvent Partition Butanol fraction | | ~510 | | Butanol enriched fraction after solvent partition with similar LC profile to that of 206A (Chloroform fraction). Mixture. |
| AAGE1-Mp288-206C Solvent Partition Water fraction | | ~400 | | Water enriched fraction after solvent partition with a different LC profile on the polar region to that of 206A and 206B. Mixture. |
| AAGE1-Mp288-207A | Hexane (100%) | ~280 | 671.4634 (−ve)<br>695.4629 (−ve) | Non-aromatic hydrocarbon, unidentified unsaturated and saturated fatty acids were observed from $^{1}$H NMR.. Mixture |
| AAGE1-Mp288-207E | Hexane:Chloroform (70:30) | ~450 | 663.4487 (+ve)<br>311.1672 (−ve)<br>325.1824 (−ve)<br>339.1986 (−ve) | Unidentified unsaturated, saturated fatty acids, saturated fatty esters, saturated hydrocarbons and triterpene were observed from $^{1}$H NMR. This fraction had similar LC but different NMR profile to that of 207A. Mixture. |
| AAGE1-Mp288-207P | Chloroform (100%) | ~580 | 217.1031 (+ve)<br>301.1392 (+ve)<br>663.4495 (+ve)<br>255.2317 (−ve)<br>283.2632 (−ve)<br>325.1831 (−ve)<br>501.3941 (−ve)<br>529.3841 (−ve) | Psoralen, psoralen analogue, saturated and unsaturated fatty acids, and other unidentified components were observed from $^{1}$H NMR. |
| AAGE1-Mp288-207Q | Chloroform:Methanol (99:1) | ~220 | 217.0498 (+ve)<br>663.4510 (+ve)<br>154.9734 (−ve)<br>433.0921 (−ve) | Mixture. Psoralen and 5-methoxypsoralen, saturated and unsaturated fatty acids, stigmasterol and β-sitosterol and other unidentified components were observed from $^{1}$H NMR. |

TABLE 7-continued

Results for active fractions from 207 series.

| Sample ID | Mobile phase (Solvent gradient) | Fraction mass (mg) | HR-ESI-MS | Comment |
|---|---|---|---|---|
| AAGE1-Mp288-207R | Chloroform:Methanol (99:1) | ~350 | 217.0499 (+ve) 301.1401 (+ve) 685.4320 (+ve) | Significant amount of 5-methoxypsoralen, trace amount of psoralen, saturated and unsaturated fatty acids, stigmasterol and β-sitosterol and other unidentified components were observed from $^{1}$H NMR. |
| AAGE1-Mp288-207S | Chloroform:Methanol (98:2) | ~670 | 217.0495 (+ve) 301.1393 (+ve) 455.0729 (+ve) 239.0592 (−ve) 255.2316 (−ve) 463.1033 (−ve) 501.3941 (−ve) 529.3841 (−ve) | Mixture. Small amount of 5-methoxypsoralen as compared to 207R, saturated and unsaturated fatty acids, stigmasterol and β-sitosterol and other unidentified components were observed from $^{1}$H NMR. |
| AAGE1-Mp288-207T | Chloroform:Methanol (98:2) | ~730 | 301.1408 (+ve) 685.4329 (+ve) 239.0591 (−ve) 325.1829 (−ve) | Mixture. Trace amount of 5-methoxypsoralen observed from HPLC profile, saturated and unsaturated fatty acids, stigmasterol and β-sitosterol and other unidentified components were observed from $^{1}$H NMR. |
| AAGE1-Mp288-207U | Chloroform:Methanol (98:2) | ~410 | 301.1403 (+ve) 483.3799 (+ve) 685.4307 (+ve) 239.0596 (−ve) 311.1690 (−ve) 325.1837 (−ve) 339.1991 (−ve) | Mixture. This fraction had similar LC and NMR profile to that of 207T, stigmasterol and β-sitosterol and other unidentified minor components were also observed from $^{1}$H NMR. |
| AAGE1-Mp288-207V | Chloroform:Methanol (98:2) | ~400 | 301.1394 (+ve) 413.3750 (+ve) 239.0590 (−ve) 255.2312 (−ve) 313.10769 (−ve) 453.3357 (−ve) 339.1991 (−ve) | Mixture Unidentified unsaturated, saturated fatty acids, stigmasterol and β-sitosterol, triterpene were observed from $^{1}$H NMR. |
| AAGE1-Mp288-207Y | Chloroform:Methanol (97:3) | ~1050 | 301.1396 (+ve) 335.2177 (+ve) 255.2320 (−ve) 293.2103 (−ve) 311.2214 (−ve) 453.3366 (−ve) | Mixture. Unsaturated fatty acids, betulinic, betulin, betulonic acids and other unidentified components were observed from $^{1}$H NMR. This fraction had similar LC and NMR profile to that of 207Z. |
| AAGE1-Mp288-207Z | Chloroform:Methanol (97:3) | ~1500 | 301.406 (+ve) 477.3320 (+ve) 615.1399 (+ve) 689.1571 (+ve) 239.6595 (−ve) 255.2320 (−ve) 453.3366 (−ve) 750.5276 (−ve) | Mixture. This fraction had similar LC and NMR profile to that of 207Y. Unsaturated fatty acids, betulinic, betulin, betulonic acids and other unidentified components were observed from $^{1}$H NMR. |
| AAGE1-Mp288-207AE | Methanol (100%) | ~650 | 615.1401 (+ve) 738.5448 (+ve) 750.5291 (−ve) 833.5178 (−ve) | Mixture. Cerebroside, saturated and unsaturated fatty acids, and other unidentified components were observed from $^{1}$H NMR. |
| AAGE1-Mp288-207W (negative activity) | Chloroform:Methanol (97:3) | ~2317 | 295.2253 (+ve) 319.2224 (+ve) 335.2176 (+ve) 413.3755 (+ve) 597.4462 (+ve) 871.5683 (+ve) 279.2323 (−ve) 293.2110 (−ve) 311.2212 (−ve) 453.3368 (−ve) | Mixture Unsaturated fatty acids (e.g. linoleic acid) were observed from 1H NMR. |

Figure 17:
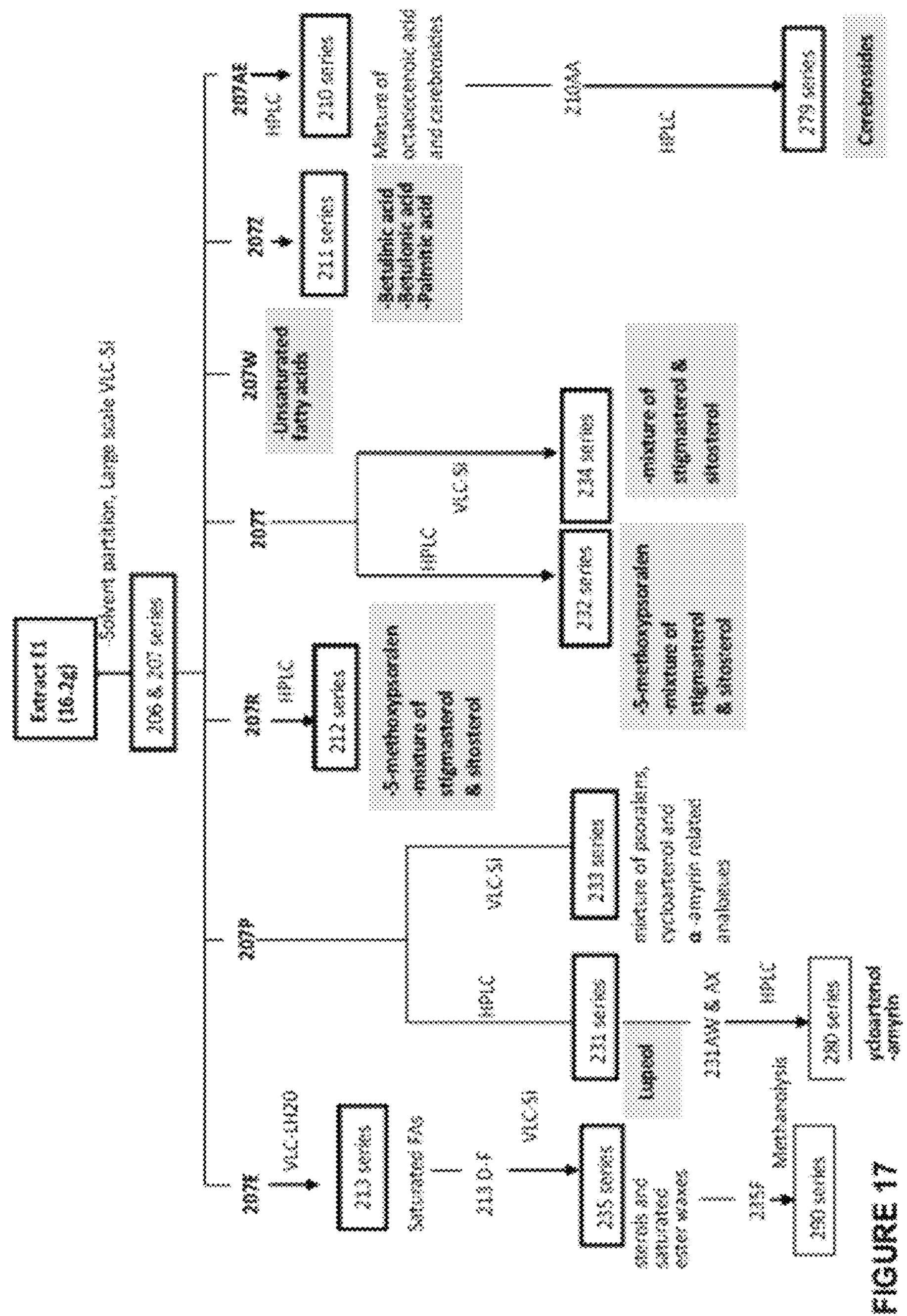
FIG. 17: Depiction of fractionation scheme for E1 (hexane extracted fraction).

To verify the presence and activity of individual compounds, further purification of fractions 207AE, 207Z, 207R, 207E, 207P and 207T was undertaken as described below. A summary of the further purification of the fractions and the compounds identified in the various sub-fractions is depicted in FIG. 17.

1. Sub-Fraction 207E 247 mg of fraction 207E was chromatographed on a Sephadex LH-20 (3×20 cm) column and eluted with pure chloroform as solvent to give twelve fractions in the 213 series of fractions (AAGE1-MP288-213A-L).

The active fractions from the sephadex column fractionation (series 213) were analysed by $^{1}$H NMR (Bruker 500 MHz) and HR-ESI-MS (Bruker microQTOF). Saturated hydrocarbon analogues, unidentified unsaturated, saturated fatty acids, triterpene, and other compounds were identified using these techniques. Highest activities based on hair follicle explant assays were observed for fractions 213D, 213E and 213F.

The combined fractions of 213D-F (120 mg) were chromatographed on a Silica gel (Merck 9385) VLC column and initially eluted with n-hexane (100% hexane, 235A and 235B, each 1 L), n-hexanedichloromethane (95:5, 235C to 0:100, 235S, each 1 L), dichloromethane-methanol (100:0, 235S to 90:10, 235V, each 1 L) and finally methanol (100% methanol, 235W, 1 L) to give 23 fractions. Fractions were dried and fractions 235E, 235F, 235G and 235H were identified as active based on hair follicle explant assays.

The active fractions from the VLC (silica gel) fractionation were analysed by $^{1}$H NMR (Bruker 500 MHz) and HR-ESI-MS (Bruker microQTOF). A mixture containing sterols and saturated ester waxes with unknown chain length were identified from the active fractions using $^{1}$H NMR results.

In particular, active fractions 235E and 235F were found to consist of four or more saturated ester waxes (hexacosyl tetracosanoate, hexacosyl hexacosanoate, hexacosyl octacosanoate and hexacosyl docosanoate) with the general structure shown below:

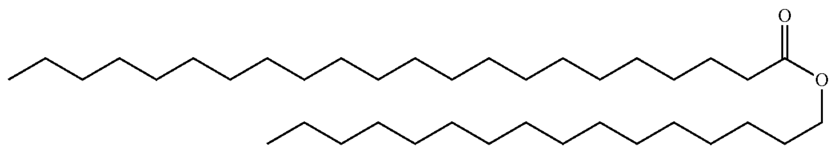 [SMILES: CCCCCCCCCCCCCCCCCCCCCC(=O)OCCCCCCCCCCCCCCCC]

Fractions 235 G and H were also identified as active. These fractions contained complex mixtures of saturated waxes and sterols.

2. Sub-Fraction 207P

Fraction 207P was further fractionated by both HPLC (methanol soluble portion) and silica VLC (chloroform soluble portion).

The methanol soluble portion of 207P (70 mg) was separated by reverse-phase preparative HPLC [Waters Xterra PrepMS, C18 Column 10 μm, 19×300 mm, gradient elution: solvent A (0.1% HCOOH in H2O): B (0.1% HCOOH in ACN) 80:20→30:70 over 90 min, 30:70→0:100 over 60 min, 0:100→0:100 over 70 min, flow rate 18 mL/min]. Fifty-five fractions (AAGE1-MP288-231A to 231BC) were collected and dried.

Fractions 231AQ, 231AW and 231AX were identified as active using hair follicle explant viability assays.

The active fractions from the HPLC fractionation were analysed by $^{1}$H NMR (Bruker 500 MHz) and HRESI-MS (Bruker microQTOF). Lupeols (C307), saturated and unsaturated fatty acids and other compounds were identified using these techniques.

Lupeol is related to betulin, tetulinic acid and betulonic acid:

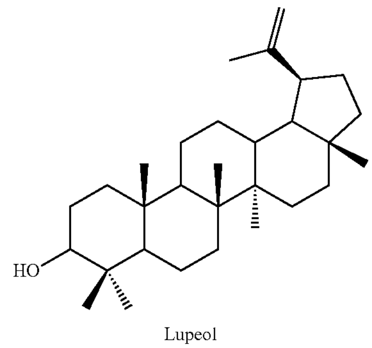

Lupeol

Fraction 231AW and 231AX (Fraction 49 and 50 of 207P-methanol soluble HPLC) (18 mg) were dissolved in methanol, combined and separated by reverse-phase preparative HPLC [Luna 5u Phenyl Hexyl column, 150×21.20 mm, gradient elution: solvent A (0.1% HCOOH in H2O): B (0.1% HCOOH in ACN) 28:72→28:72 over 100 min, 28:72→17:83 over 80 min, 17:83→0:100 over 20 min, 0:100→0:100 over 14 min, flow rate 18 mL/min]. Thirty seven fractions (AAGE1-MP288-280A to 280AK) were collected and dried.

Fractions 280U and 280AH were identified as active.

The active fractions from the HPLC fractionation were analysed by 1H NMR (Bruker 500 MHz) and HRESI- MS (Bruker microQTOF). Mixtures containing cycloartenol, α-amyrin and related analogues were identified in the active fractions using these techniques.

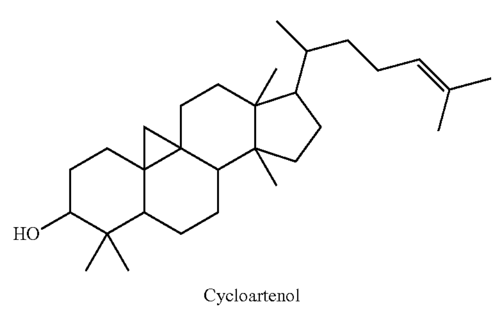

Cycloartenol

-continued

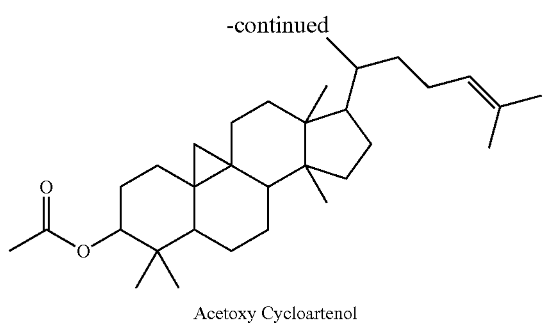

Acetoxy Cycloartenol

Furthermore, the chloroform soluble portion of 207P (350 mg) was chromatographed on a Silica gel (Merck 9385) VLC column and initially eluted with n-hexane (100% hexane, 233A, 1 L), n-hexane-dichloromethane (80:20, 233B to 0:100, 233N, each 1 L), dichloromethane-methanol (100:0, 233N to 90:10, 233W, each 1 L) and finally methanol (100% methanol, 233X, 1 L) to give 24 fractions. Fraction 233G was identified as the most active fraction.

The active fraction 233G from the VLC (silica gel) fractionation was analysed by 1H NMR (Bruker 500 MHz) and HR-ESI-MS (Bruker microQTOF). A mixture of psoralens, sterols, saturated and unsaturated fatty acids and other compounds were identified in this fraction.

3. Sub-Fraction 207R

The DMSO/methanol extract (45.6 mg) was separated by reverse-phase preparative HPLC [Waters Xterra PrepMS, C18 Column 10 μm, 19×300 mm, gradient elution: solvent A (0.1% HCOOH in H2O): B (0.1% HCOOH in ACN) 80:20→30:70 over 120 min, 30:70→0:100 over 60 min, 0:100→0:100 over 40 min flow rate 18 mL/min. Twenty seven fractions (AAGE1-MP288-212A to 212AA) were collected and dried. Fractions 212 D-F were identified as active with fractions 212R, S and Y showing weak activity.

The active fractions from the HPLC fractionation were analysed by $^{1}$H NMR (Bruker 500 MHz) and HRESI-MS (Bruker microQTOF). The inactive fraction 212G was also analysed. 5-methoxypsoralen (C288), analogues of stigmasterol and β-sitosterol, saturated and unsaturated fatty acids and other compounds were identified using these techniques.

4. Sub-Fraction 207T

Sub-fraction 207T was further fractionated by both HPLC (methanol soluble portion) and silica VLC (chloroform soluble portion).

The methanol soluble portion of 207T (20 mg) was separated by reverse-phase preparative HPLC [Waters Xterra PrepMS, C18 Column 10 μm, 19×300 mm, gradient elution: solvent A (0.1% HCOOH in H2O): B (0.1% HCOOH in ACN) 90:10→30:70 over 90 min, 30:70→0:100 over 60 min, 0:100→0:100 over 70 min, flow rate 18 mL/min. Twenty three fractions (AAGE1-MP288-232A to 232W) were collected and dried.

Fractions 232E, 232F, 232G, 232P and 232Q were identified as active.

The active fractions from the HPLC fractionation were analysed by 1H NMR (Bruker 500 MHz) and HRESI-MS (Bruker microQTOF). 5-methoxypsoralens (C288), stigmasterol (N58), β-sitosterol (C293), saturated and unsaturated fatty acids and other compounds were identified using these techniques.

Further, the chloroform soluble portion of 207T (640 mg) was chromatographed on a Silica gel (Merck 9385) VLC column and initially eluted with n-hexane (100% hexane, 234A, 1 L), n-hexane-dichloromethane (50:50, 234B to 0:100, 234L, each 1 L), dichloromethane-ethyl acetate (90:10, 234M to 70:30, 234N, each 1 L), dichloromethane-methanol (99.5:0.5, 234O to 10:90, 234T, each 1 L) and finally methanol (100% methanol, 234U, 1 L) to give 21 fractions.

Fractions 234G and 234H were identified as active.

The active fractions 234G and 234H were analysed by 1H NMR (Bruker 500 MHz) and HR-ESI-MS (Bruker microQTOF). A mixture containing stigmasterol and β-sitosterol was identified in this fraction using these techniques. The compounds, sitosterol and stigmasterol were present in the following ratios:

234H: Sitosterol-76.6%+Stigmasterol-23.5%

234G: Sitosterol-80.2%+Stigmasterol-19.8%

5. Sub-Fraction 207Z

The DMSO/methanol extract (72 mg) was separated by reverse-phase preparative HPLC [Waters Xterra PrepMS, C18 Column 10 μm, 19×300 mm, gradient elution: solvent A (0.1% HCOOH in H2O): B (0.1% HCOOH in ACN) 70:30→60:40 over 30 min, 60:40→20:80 over 90 min, 20:80→0:100 over 60 min, 0:100→0:100 over 40 min flow rate 18 mL/min. Thirty nine fractions (AAGE1-MP288-211A to 210AM) were collected and dried.

Fraction 211A, 221S, 211V and 211AM were identified as the most active.

The active fractions from the HPLC fractionation were analysed by 1H NMR (Bruker 500 MHz) and HRESI-MS (Bruker microQTOF). Several inactive and weakly active fractions were analysed to help understand structure activity relationships (SAR). Palmitic acid (C292), octadecenoic acid, saturated and unsaturated fatty acids, betulinic (C296), betulin, betulonic acids (C295) and other compounds were identified using these techniques.

In particular, sub-fraction 211S contained betulinic acid as the major compound:

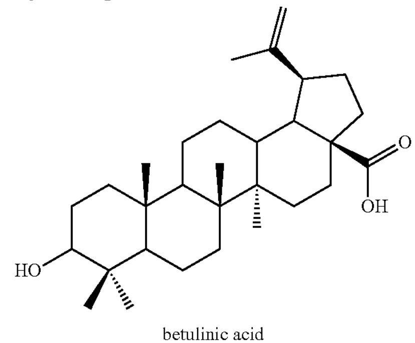

betulinic acid

Sub-fraction 211V contained betulonic acid as the major compound:

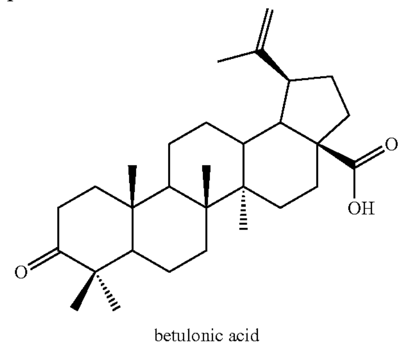

betulonic acid

Sub-fraction 211Z contained palmitic acid as the major compound:

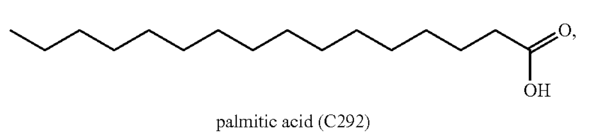 [SMILES: CCCCCCCCCCCCCCCC(=O)O]

palmitic acid (C292)

6. Sub-Fraction 207AE

The DMSO/methanol extract (80 mg) of fraction 207AE was separated by reverse-phase preparative HPLC [Waters Xterra PrepMS, C18 Column 10 μm, 19×300 mm, gradient elution: solvent A (0.1% HCOOH in H2O): B (0.1% HCOOH in ACN) 85:15→60:40 over 30 min, 60:40→30:70 over 90 min, 30:70→0:100 over 60 min, 0:100→0:100 over 40 min flow rate 18 mL/min. Twenty eight fractions (AAGE1-MP288-210A to 210AB) were collected and dried.

Fractions 210L and 201AA were identified as active.

The active fractions from the HPLC fractionation were analysed by 1H NMR (Bruker 500 MHz) and HRESI-MS (Bruker microQTOF). Several inactive fractions were also analysed to help understand SAR amongst the unsaturated fatty acids represented in this series. Trihydroxy octadecenoic acid, dihydroxy octadecenoic acid, saturated and unsaturated fatty acids, cerebrosides, and other compounds were identified using these techniques.

Analysis of the second most active fraction, 210L by 1H NMR and HR-ESI-MS, confirmed the presence of 13-Hydroxy-9,11-octadecadienoic acid as the major compound. The structure is consistent with the 1H NMR data obtained.

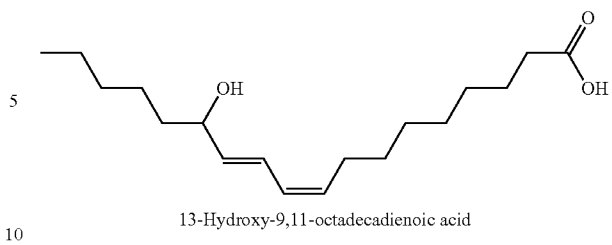

13-Hydroxy-9,11-octadecadienoic acid

The fraction with the highest activity and highest weight (fraction 210AA) consists largely of glucosylceramide.

Fraction 210AA was further fractionated by HPLC as follows: Fraction 210AA (from the HPLC of 207AE) (15 mg) was dissolved in methanol and separated by reverse-phase preparative HPLC [Luna 5u Phenyl Hexyl column, 150×21.20 mm, gradient elution: solvent A (0.1% HCOOH in H2O): B (0.1% HCOOH in ACN) 40:60→25:75 over 100 min, 25:75→0:100 over 40 min, 0:100→0:100 over 20 min, flow rate 18 mL/min]. Twenty-nine fractions (AAGE1-MP288-279A to 279AC) were collected and dried.

Fractions 279E, 279O and 279U were identified as active.

The active fractions from the HPLC fractionation were analysed by 1H NMR (Bruker 500 MHz) and HRESI-MS (Bruker microQTOF). Cerebrosides, β-sitosterol analogues, and other compounds were identified using these techniques.

The fraction with highest total HF explant viability promoting activity, 279U was analysed with 1H NMR and HR-ESI-MS, revealing it to contain a mixture of two cerebrosides with cis(8Z) and trans(8E) confirmations on C-8 of the double bond. The most likely structures are shown below:

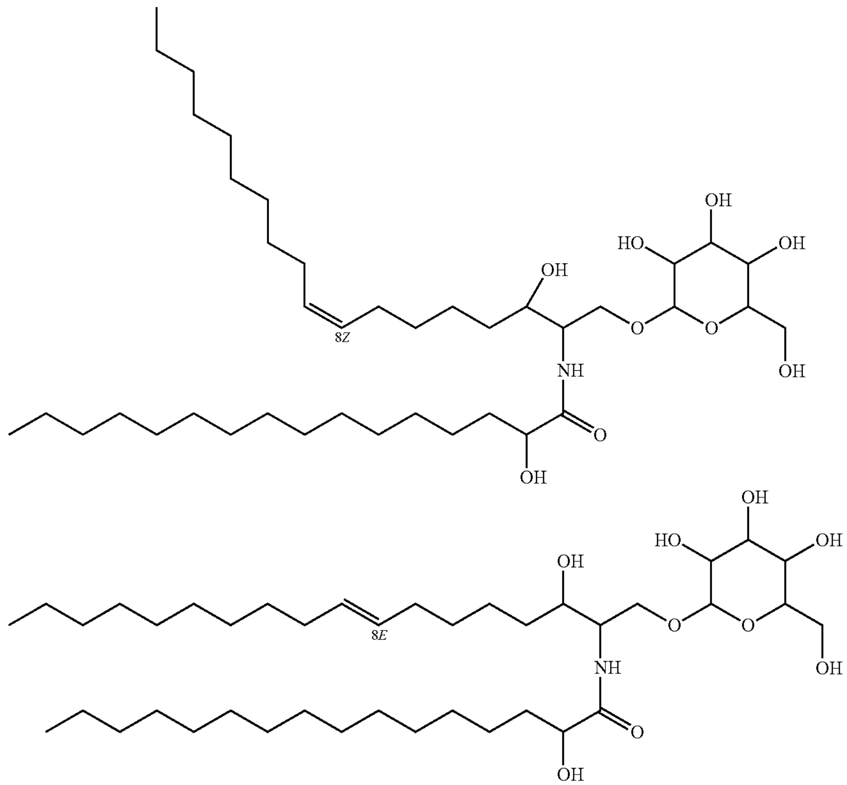

Cerebrosides.

Top, cis-conformation; bottom, trans-conformation

Relative Abundance

The relative amounts of each compound present in the 16.2 g of crude E1 extract were estimated and are summarized in Table 8. The percentage ratio is based only on the weights of compounds purified from fractions that were selected for further analysis. Adjacent fractions from the large scale fractionation of crude E1 extract (207 series) might also contain the compounds of interest but this will not have been taken into account when calculating relative amount (%). The values in Table 8 are likely to be underestimates of the true relative abundance of the compounds within the entire sample.

TABLE 8

Relative amounts of respective compounds in crude E1 extract

| Compound | *Relative amount (w/w %) of compound in crude E1 extract |
|---|---|
| Lupeol (C307) | 0.31 |
| Cycloartenol | 0.43 |
| α-Amyrin | 0.43 |
| Saturated ester waxes | 0.74 |
| 5-methoxypsoralen (C288) | 1.23 |
| Mixture of stigmasterol (N58) and β-sitosterol (C293) | 5.56 |
| Betulinic acid (C296) | 0.37 |
| Betulonic acid (C295) | 0.80 |
| Palmitic acid (C292) | 0.46 |
| 13-Hydroxy-9,11-octadecadienoic acid (C294) | 0.19 |
| Cerebrosides | 0.49 |
| Unsaturated fatty acids (fatty acids similar to those from 207W)** | 18.52 |

Example 11

Topical Application of TR3

Fraction 207W of E1 was removed because it was not shown to be beneficial for hair growth. Fraction 207W contains 85-90% unsaturated fatty acids. E1 was reconstituted from the 207 series of fractions minus fraction 207W to provide TR3. The composition of TR3 is described in Table 9. Note that the fractional weights listed in Table 9 are approximate weights.

TABLE 9

Composition of TR3 (total mass of TR3 = 13055 mg)

| Sample ID | Mobile phase (%) (Solvent gradient) | Fraction mass (mg) | TR3 (%) |
|---|---|---|---|
| 207A | Hexane 100 | 280 | 2% |
| 207B | Hexane:Chloroform (80:20) | 20 | 0.15% |
| 207C | Hexane:Chloroform (80:20) | 60 | 0.49% |
| 207D | Hexane:Chloroform (75:25) | 240 | 2% |
| 207E | Hexane:Chloroform (70:30) | 450 | 4% |
| 207F | Hexane:Chloroform (65:35) | 280 | 2% |
| 207G | Hexane:Chloroform (60:40) | 200 | 2% |
| 207H | Hexane:Chloroform (50:50) | 480 | 4% |
| 207I | Hexane:Chloroform (45:55) | 680 | 6% |
| 207J | Hexane:Chloroform (40:60) | 150 | 1% |
| 207K | Hexane:Chloroform (30:70) | 95 | 1% |
| 207L | Hexane:Chloroform (30:70) | 140 | 1% |
| 207M | Hexane:Chloroform (25:75) | 190 | 1% |
| 207N | Hexane:Chloroform (20:80) | 230 | 2% |
| 207O | Hexane:Chloroform (10:90) | 220 | 2% |
| 207P | Chloroform 100 | 580 | 4% |
| 207Q | Chloroform:Methanol (99:1) | 220 | 2% |
| 207R | Chloroform:Methanol (99:1) | 350 | 3% |
| 207S | Chloroform:Methanol (99:2) | 670 | 5% |
| 207T | Chloroform:Methanol (98:2) | 730 | 6% |
| 207U | Chloroform:Methanol (98:2) | 410 | 3% |
| 207V | Chloroform:Methanol (98:2) | 400 | 3% |
| 207X | Chloroform:Methanol (97:3) | 920 | 7% |
| 207Y | Chloroform:Methanol (97:3) | 1050 | 8% |
| 207Z | Chloroform:Methanol (97:3) | 1500 | 11% |
| 207AA | Chloroform:Methanol (95:5) | 400 | 3% |
| 207AB | Chloroform:Methanol (90:10) | 260 | 2% |
| 207AC | Chloroform:Methanol (80:20) | 780 | 6% |
| 207AD | Chloroform:Methanol (50:50) | 420 | 3% |
| 207AE | Methanol 100 | 650 | 5% |

A total of 26 μg TR3 was applied topically once a day to the five hair loss zones (1R, 1L, 1M, 2M and 3M) to 20 patients suffering from varying degrees of hair loss (class 2 to class 7).

Figure 18:
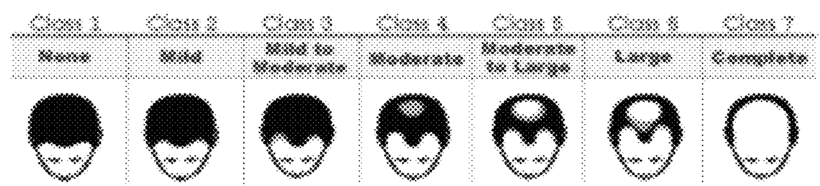
FIG. 18. The Norwood scale of hair loss.

Four subjects with class 2 hair loss, two subjects with class 3 hair loss, two subjects with class 4 hair loss, two subjects with class 5 hair loss, six subjects with class 6 hair loss and four subjects with class 7 hair loss were studied for a total of 20 subjects. Hair loss classifications are depicted in FIG. 18.

Hair growth was measured as a hair density measurement (hairs per $cm^2$) before (Month 0) and after treatment for 1 (M1) and 3 months (M3) respectively. Two trichometric systems (camera and software) were used to quantify hair growth:

1. TricoScan (automated system) and
2. Folliscope (manual system).

In both systems, vellus/miniaturized hair (VH) was defined as hair with a diameter of less than 40 μm diameter and terminal hair (TH) was defined as hair with a diameter of more than 40 μm.

In hair loss classes 2 to 6, the Tricoscan system was used for measurement in all hair zones. In zone 3, measurements were additionally made manually using a Folliscope. In hair loss class 7, all measurements were performed with a Folliscope.

Figure 19:
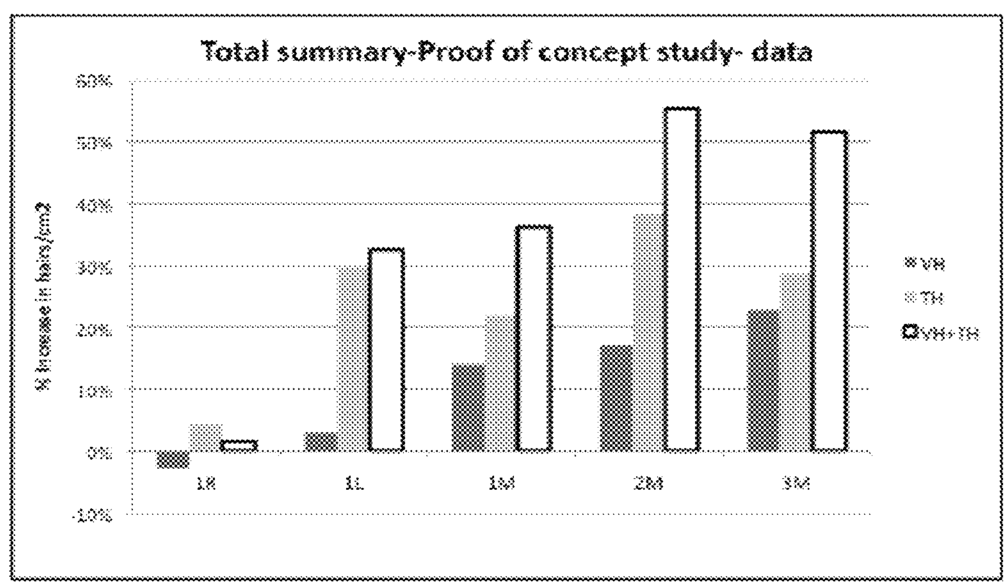
FIG. 19. Percentage increase in hair density in scalp zones 1R, 1L, 1M, 2M and 3M following three months of treatment with TR3. Results averaged over 20 subjects.

FIG. 19 summarizes the cumulative results for each scalp zone 1R, 1L, 1M, 2M and 3M after 3 months of treatment with TR3. The percent increase in the number of vellus and miniaturized (VH) hair and terminal hair (TH) and total hair (VH+TH) per $cm^2$ is averaged for each of the 20 subjects.

Individual hair follicles were tracked for two subjects, N.P. (zone 2M) and S.L. (zone 3M) over 3 months (Tables 10 and 11). Thicker hairs, new hairs and telogenic hairs were counted. The number of net new hairs (new hairs grown due to the application of TR3 as opposed to new hairs grown due to the normal hair cycle) was determined by taking the number of telogenic hairs into account at each time point.

The hair cycle is defined by three phases—the anagen (growth phase), catagen (transition phase) and telogen (resting or quiescent phase). For the purposes of this exercise, miniaturized hair that has regressed or been lost from the previous time point due to hair follicle cycling is counted as telogenic hair.

With reference to Tables 10 and 11, at month 1 and month 3, a number of new hairs have appeared. However, some of the new hairs are due to the fact at a prior point in time (time 0), the hairs had disappeared (gone into telogen phase) and have now reappeared. These new hairs cannot be attributed to the application of TR3.

However, when analyzing the microphotography, it is not possible to determine which hairs were in telogen at time 0. It is only possible to see at month 1 or month 3 how many hairs have "disappeared" into telogen. Therefore, the number of hairs that have disappeared/been lost into telogen phase from time zero to month 3 is used as an estimate of the number of hairs that would be expected to have cycled from telogen to anagen over the same time period.

Therefore the number of net new hairs due to the application of TR3 is determined by deducting the total number of new hairs over the time period by the number of telogenic hairs over the same time period:

Net new hair=total number of new hairs (number of hairs at month 3−number of hairs at time 0)−total number of hairs lost (telogenic hair)

The following results were observed (Tables 10 and 11):

TABLE 10

Zone 3M (S.L): Study of 140 Hair Follicular Units (HF) in Zone 3M containing 266 hairs over 3 months of treatment with TR3

| thicker hairs | new hairs | telogen hairs | net new hairs |
|---|---|---|---|
| Month-1 | | | |
| 31 | 45 | 29 | 16 |
| Month-3 | | | |
| 52 | 49 | 26 | 23 |
| Month-3 (Cumulative) | | | |
| 83 (31%) | 94 | 55 | 39 (15%) |

Net effects:
Hair thickening: 83 hairs (31%)
Net New hairs (total new hairs − telogen hairs): 39 hairs (15%)
New hairs + Hair thickening: 46%

TABLE 11

Zone 2M (N.P.): Study of 163 Hair Follicular Units (HF) in Zone 2M containing 316 hairs over 3 months of treatment with TR3

| thicker hairs | new hairs | telogen hairs | net new hairs |
|---|---|---|---|
| Month-1 | | | |
| 42 | 21 | 8 | 13 |
| Month-3 | | | |
| 67 | 21 | 10 | 11 |
| Month-3 (Cumulative) | | | |
| 109 | 42 | 18 | 24 (8%) |

Net effects:
Hair thickening: 109 hairs (34%)
Net New hairs (total new hairs − telogen hairs): 24 hairs (8%)
New hairs + Hair thickening: 133 hairs (42%)

Example 12

Extracts, Fractions, Sub-Fractions and Purified Compounds from *Ficus* Exhibit Synergism The active extracts, fractions, sub-fractions and purified compounds of the invention are investigated for synergism using the hair follicle explant viability assay described in Example 7.

The hair follicle explant assays compare an untreated control to treatments containing single extracts and to treatments containing different combinations of the various extracts, fractions, sub-fractions and compounds purified therefrom. Combinations of the extracts, fractions, sub-fractions and compounds purified therefrom have a positive synergistic effect on hair follicle explant viability.

Various combinations are tested in patients to show potency in treating hair loss. Specifically, a suitable preparation containing the combination of interest is applied to specific scalp zones in the range of 1 μg/ml-10 mg/ml in the treatment group. The control group is treated with the pharmaceutical carrier only while a third group is treated with 5% minoxidil. The tested groups include patients presenting with different classes of hair loss and/or of different ethnic backgrounds. Increase in hair density is assessed after 3 to 6 months or 8 to 12 months of treatment with trichometry.

Specific combinations of the extracts, fractions, sub-fractions and compounds purified thereform of the invention are useful for increasing hair loss or preventing hair loss by administering compositions comprising the combinations to a patient. Combinations of the extracts, fractions, sub-fractions and compounds of the invention are useful for treating different hair loss zones of the scalp and for treating subjects presenting with varying classes of hair loss and/or of varying ethnic backgrounds.

REFERENCES

Blanpain, C. and E. Fuchs. (2006) Epidermal stem cells of the skin. *Annu. Rev. Cell Dev. Biol.* 22:339-373.

Channabasavaraj K. P., Badami S. & Bhojraj S. (2008) Hepatoprotective and antioxidant activity of methanol extract of *Ficus glomerata. Nat. Med.*(*Tokyo*) 62, 379-383.

Cotsarelis, G. and S. E. Millar. 2001. Towards a molecular understanding of hair loss and its treatment. *Trends Mol. Med.* 7:293-301.

Garba S. H., Prasad J. & Sandabe U. K. (2006) Histomorphological effect of the aqueous root-bark extract of fius sucomorus (linn) on the liver and kidney of albino rats. *International Journal of Pharmacology* 2, 628-632.

Kala C. P., Farooquee N. A. & Dhar U. (2004) Prioritization of medicinal plants on the basis of available knowledge, existing practices and use value status in Uttaranchal, India. Biodiversity and Conservation 13, 453-469.

Liqing Z., Bochu W., Jing Z., Lingxi C., Chuanyun D. & Chuanren D. (2005) Protoplast isolation of callus in *Echinacea augustifolia. Colloids Surf. B Biointerfaces* 44, 1-5.

Morris, R. J., Y. Liu, L. Marles, Z. Yang, C. Trempus, S. Li, J. S. Lin, J. A. Sawicki, and G. Cotsarelis. (2004) Capturing and profiling adult hair follicle stem cells. *Nat. Biotechnol.* 22:411-417.

Sokmen M., Serkedjieva J., Daferera D., Gulluce M., Polissiou M., Tepe B., Akpulat H. A., Sahin F. & Sokmen A. (2004) In vitro antioxidant, antimicrobial, and antiviral activities of the essential oil and various extracts from herbal parts and callus cultures of *Origanum acutidens. J. Agric. Food Chem.* 52, 3309-3312.

Tucker, M. R. and T. Laux. (2007) Connecting the paths in plant stem cell regulation. *Trends Cell Biol.* 17:403-410.

We claim:

1. A method of producing a composition, useful as a hair growth increasing agent and/or a hair loss decreasing agent, said method comprising:

(a) extracting an aerial root portion of a *Ficus* plant with n-hexane to obtain a n-hexane fraction, (b) partitioning the n-hexane fraction with chloroform to obtain a chloroform partitioned fraction;

(c) loading the chloroform partitioned fraction into a chromatography column, (d) eluting the chloroform partitioned fraction through sequential elution using solvent mixtures from 100% hexane to 100% chloroform to 100% methanol to obtain a plurality of sub-fractions, and (e) collecting and combining the plurality of sub-fractions to obtain the composition.

2. The method of claim 1, wherein the *Ficus* plant is *Ficus Benghalensis*.

3. The method of claim 1, wherein the solvent mixtures used in the eluting step comprise: 100% hexane, 80% hexane: 20% chloroform, 75% hexane:25% chloroform, 70% hexane: 30% chloroform, 65% hexane:35% chloroform, 60% hexane: 40% chloroform, 50% hexane:50% chloroform, 45% hexane: 55% chloroform, 40% hexane:60% chloroform, 30% hexane: 70% chloroform, 25% hexane:75% chloroform, 20% hexane: 80% chloroform, 10% hexane:90% chloroform, 100% chloroform, 99% chloroform:1% methanol, 98% chloroform:2% methanol, 97% chloroform:3% methanol, 95% chloroform:5% methanol, 90% chloroform:10% methanol, 80% chloroform:20% methanol, 50% chloroform:50% methanol and 100% methanol.

4. The method of claim 1, wherein the solvent mixtures used in the eluting step do not include 97% chloroform: 3% methanol.

5. The method of claim 1, wherein the aerial root portion of the *Ficus* plant is dried prior to extraction with n-hexane.

6. A composition useful as a hair growth increasing agent and/or a hair loss decreasing agent obtained by:

(a) extracting an aerial root portion of a *Ficus* plant with n-hexane to obtain a n-hexane fraction, (b) partitioning the n-hexane fraction with chloroform to obtain a chloroform partitioned fraction;

(c) loading the chloroform partitioned fraction into a chromatography column, (d) eluting the chloroform partitioned fraction through sequential elution using solvent mixtures from 100% hexane to 100% chloroform to 100% methanol to obtain a plurality of sub-fractions, and (e) collecting and combining the plurality of sub-fractions to obtain the composition.

7. The composition of claim 6, wherein the composition further comprises a carrier.

8. A method for increasing hair growth or decreasing hair loss in a mammal wherein the method comprises administering the composition of claim 7 to the mammal.

9. The method of claim 8, wherein the method comprises-administering 1 to 100 μg of the composition per day.

10. A method of increasing the viability of a hair follicle cell, wherein the method comprises contacting the hair follicle cell with the composition of claim 7.

11. The composition of claim 6, wherein the composition comprises sub-fractions eluted using each of the following solvent mixtures: 100% hexane, 80% hexane:20% chloroform, 75% hexane:25% chloroform, 70% hexane:30% chloroform, 65% hexane:35% chloroform, 60% hexane:40% chloroform, 50% hexane:50% chloroform, 45% hexane:55% chloroform, 40% hexane:60% chloroform, 30% hexane:70% chloroform, 25% hexane:75% chloroform, 20% hexane:80% chloroform, 10% hexane:90% chloroform, 100% chloroform, 99% chloroform:1% methanol, 98% chloroform:2% methanol, 97% chloroform:3% methanol, 95% chloroform: 5% methanol, 90% chloroform:10% methanol, 80% chloroform:20% methanol, 50% chloroform:50% methanol and 100% methanol.

12. The composition of claim 6, wherein the composition does not contain a sub-fraction eluted at 97% chloroform: 3% methanol.

13. The composition of claim 6, wherein the composition does not contain a sub-fraction comprising 85-90% unsaturated fatty acids.

14. The composition of claim 6, wherein the composition comprises one or more of the following compounds selected from: lupeol, cycloartenol, α-amyrin, saturated ester wax, 5-methoxypsoralen, stigmasterol, β-sitosterol, betulinic acid, betulonic acid, palmitic acid, 13-hydroxy-9,11-octadecadieonic acid and cerebrosides.

15. The composition of claim 6, wherein the composition comprises one or more of the following compounds selected from: at least 0.3% by weight lupeol, at least 0.4% by weight cycloartenol, at least 0.4% by weight α-amyrin, at least 0.7% by weight saturated ester wax, at least 1.2% by weight 5-methoxypsoralen, at least 5% by weight stigmasterol and β-sitosterol, at least 0.3% by weight betulinic acid, at least 0.8% by weight betulonic acid, at least 0.46% by weight palmitic acid, at least 0.1% by weight 13-hydroxy-9,11-octadecadieonic acid and at least 0.4% by weight cerebrosides.

16. The composition of claim 6, wherein the composition comprises lupeol, cycloartenol, α-amyrin, saturated ester wax, 5-methoxypsoralen, stigmasterol, β-sitosterol, betulinic acid, betulonic acid, palmitic acid, 13-hydroxy-9,11-octadecadieonic acid and cerebrosides.

17. The composition of claim 6, wherein the composition comprises at least 0.3% by weight lupeol, at least 0.4% by weight cycloartenol, at least 0.4% by weight α-amyrin, at least 0.7% by weight saturated ester wax, at least 1.2% by weight 5-methoxypsoralen, at least 5% by weight stigmasterol and β-sitosterol, at least 0.3% by weight betulinic acid, at least 0.8% by weight betulonic acid, at least 0.46% by weight palmitic acid, at least 0.1% by weight 13-hydroxy-9, 11-octadecadieonic acid and at least 0.4% by weight cerebrosides.

18. The composition of claim 6, wherein the aerial root portion of the *Ficus* plant is dried prior to extraction with n-hexane.

* * * * *